United States Patent [19]

Petrzilka et al.

[11] Patent Number: 4,595,521
[45] Date of Patent: Jun. 17, 1986

[54] PYRIDAZINE DERIVATIVES USEFUL AS COMPONENTS OF LIQUID CRYSTAL MIXTURES

[75] Inventors: Martin Petrzilka, Kaiseraugst, Switzerland; Georg Trickes, Grenzach-Wyhlen, Fed. Rep. of Germany

[73] Assignee: Hoffmann-La Roche Inc., Nutley, N.J.

[21] Appl. No.: 551,655

[22] Filed: Nov. 14, 1983

[30] Foreign Application Priority Data

Nov. 19, 1982 [CH] Switzerland .................. 6748/82
Jan. 14, 1983 [CH] Switzerland .................. 208/83
Sep. 21, 1983 [CH] Switzerland .................. 5132/83

[51] Int. Cl.[4] .................. C09K 3/34; G02F 1/13; C07D 237/02; C07D 237/08
[52] U.S. Cl. .................. 252/299.61; 252/299.5; 350/346; 350/350 R; 544/224; 544/239
[58] Field of Search .................. 544/224, 239; 252/299.61, 299.5; 350/350 R, 346

[56] References Cited

U.S. PATENT DOCUMENTS

| | | | |
|---|---|---|---|
| 3,931,041 | 1/1976 | Saeva et al. | 350/350 R |
| 4,066,570 | 1/1978 | Boller et al. | 424/37 |
| 4,419,262 | 12/1983 | Petrzilka | 544/224 |
| 4,439,015 | 3/1984 | Rich et al. | 350/350 R |
| 4,452,718 | 6/1984 | Schadt et al. | 544/239 |
| 4,460,770 | 7/1984 | Petrzilka et al. | 350/350 R |
| 4,482,472 | 11/1984 | Carr et al. | 252/299.1 |
| 4,512,636 | 4/1985 | Andrews et al. | 350/350 R |

FOREIGN PATENT DOCUMENTS

| | | |
|---|---|---|
| 56501 | 7/1982 | European Pat. Off. |
| 3221462 | 1/1983 | Fed. Rep. of Germany |
| 3237367 | 4/1983 | Fed. Rep. of Germany .................. 252/299.63 |
| 2102803A | 2/1983 | United Kingdom |

OTHER PUBLICATIONS

Brown, Analytical Chemistry, vol. 41, No. 13, (1969) pp. 26–39.
Demus, Non Emissive Electrooptic Displays, Plenum Press, 1979, New York, pp. 83–119.
Yoshihito, et al., Heterocycl., 9 (1978) 1397.
Oshwa, et al., Chem. Pharm. Bull., 26, (1978) 2428.
J. A. Nash, et al., Mol. Cryst. Liq. Cryst., 25 (1974) 299.
H. Schubert, et al., Z. Chemie, 6 (1966) 467, and its Chem. Abst., 66:54977e (1967).
C. Weygand, et al., J. Prakt. Chemie, 151 (1938) 221, and its Chem. Abst., 33:153(3) (1938).
H. Zaschke, et al., Z. Chemie, 17 (1977) 333, and its Chem. Abst., 88:6824K (1978).
H. Zaschke, et al., J. Prakt. Chemie, 321 (1979) 629, and its Chem. Abst., 92:58707b (1980).

*Primary Examiner*—Donald G. Daus
*Assistant Examiner*—William A. Teoli, Jr.
*Attorney, Agent, or Firm*—Jon S. Saxe; Bernard S. Leon; George W. Johnston

[57] ABSTRACT

Compounds of the formula

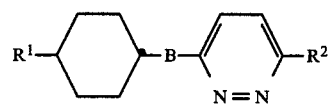

I wherein B is —C≡C— or —CH$_2$CH$_2$—, R$^1$ is straight-chain C$_1$–C$_{12}$-alkyl and R$^2$ is straight-chain C$_1$–C$_{12}$-alkyl or straight-chain C$_1$–C$_{12}$-alkoxy, their manufacture and use in liquid crystalline mixtures are described.

16 Claims, No Drawings

PYRIDAZINE DERIVATIVES USEFUL AS COMPONENTS OF LIQUID CRYSTAL MIXTURES

BACKGROUND OF THE INVENTION

1. Field of the Invention

This invention relates to liquid crystalline compounds and mixtures.

2. Description

Liquid crystals have recently gained considerable importance as dielectrics in indicating devices, since the optical properties of such substances can be influenced by an applied voltage. Electro-optical devices based on liquid crystals are well known to the person skilled in the art and can be based on various effects.

The dielectric anisotropy $\Delta\epsilon$ of a compound or mixture is the difference between the dielectric constant along the longitudinal molecular axis ($\epsilon_\parallel$) and the dielectric constant perpendicular thereto ($\epsilon_\perp$). In the case of non-liquid crystalline components the term "dielectric anisotropy" in the scope of the present invention signifies the extrapolated value (from liquid crystalline mixtures which contain this component) of the dielectric anisotropy at a temperature which lies 10° C. below the extrapolated (virtual) clearing point.

Nematic and cholesteric liquid crystals with negative anisotropy of the dielectric constants ($\Delta\epsilon = \epsilon_\parallel - \epsilon_\perp < 0$) are orientated in an electric field with their longitudinal molecular axes perpendicular to the field direction. This effect is known and is used for the control of the optical transmissivity in various liquid crystal indicators, for example in liquid crystal cells of the light scattering type (dynamic scattering), of the so-called DAP type (deformation of aligned phases) or of the guest/host type (guest host interaction).

These "guest/host cells" comprise essentially a condenser, at least one electrode being transparent and the dielectric being formed from a nematic or cholesteric liquid crystal which contains one or more dichroic colouring substances. Since the usable colouring substances mainly have positive dichroism, i.e. the transition moment of the absorption of visible light lies approximately in the direction of the longitudinal molecular axis, the orientation of the liquid crystal with the molecular axes parallel to the surface of the plates generally corresponds to the coloured state and the homeotropic orientation (longitudinal molecular axes perpendicular to the surface of the plates) generally corresponds to the colourless condition of the cell. When a liquid crystal with positive dielectric anisotropy is used, its homogeneous orientation (which is achieved by treating the surface of the plates) is arranged homeotropic by the application of a voltage, i.e. the cell is switched from "coloured" to "colourless". In this manner colourless symbols are shown on a coloured background. On the other hand, when a liquid crystal with negative dielectric anisotropy is used, its homeotropic orientation (which is achieved by treating the surface of the plates) is arranged parallel to the electrode surfaces by the application of a voltage, whereby the reading of coloured image elements on a colourless background is made possible.

Further, for the improvement of the multiplex ratio in the multiplex control of liquid crystal indicators, especially of rotation cells and guest/host cells, there has been proposed a two-frequency matrix addressing (e.g. German Offenlegungsschriften 2,856,134 (Great Britain Pat. No. 2,013,014) and 2,907,940 (Great Britain Pat. No. 2,020,075)). In this case, use is made of the fact that the dielectric anisotropy of liquid crystals, which upon application of a low-frequency voltage have a positive anisotropy of the dielectric constants, is negative in the case of high frequencies. In order to maintain the capacitive loss at a low level, the "cross-over frequency $f_c$ (dielectric relaxation frequency at which $\epsilon_\parallel = \epsilon_\perp$) of such liquid crystals should be as low as possible and should not lie above about 20 kHz. Further, the total sum of the dielectric anisotropies should be as large as possible not only below but also above the cross-over frequency. It has, however, been found that the substances, which are especially suitable for the two-frequency addressing, at frequencies above the cross-over frequency generally have a smaller absolute dielectric anisotropy than below the cross-over frequency. This disadvantage can be eliminated by adding compounds with negative dielectric anisotropy and suitable relaxation behaviour.

A series of liquid crystalline compounds with weakly negative dielectric anisotropy is already known. On the other hand, still relatively few liquid crystal components with large negative anisotropy of the dielectric constants are known. Moreover, the latter generally have disadvantages such as, for example, poor solubility in mixtures, high viscosity, high melting points, strong smectic tendencies, chemical instability or large melting point depressions in mixtures. There accordingly exists a need for further compounds with negative dielectric anisotropy which allow the properties of mixtures for the widest variety of electro-optical applications to be improved.

The present invention provides novel liquid crystalline compounds and mixtures with such improved properties.

SUMMARY OF THE INVENTION

The present invention is concerned with novel pyridazine derivatives of the formula

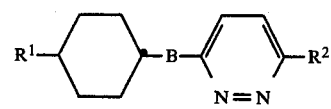

wherein B is $-C\equiv C-$ or $-CH_2CH_2-$, $R^1$ is straight-chain $C_1-C_{12}$-alkyl and $R^2$ is straight-chain $C_1-C_{12}$-alkyl or straight-chain $C_1-C_{12}$-alkoxy.

The invention is also concerned with the manufacture of the compounds of the formula I above, liquid crystalline mixtures which contain these compounds as well as their use in electro-optical devices.

It has now been found that the compounds of formula I have a dielectric anisotropy of about $-9$, a good solubility in known liquid crystal mixtures and a low viscosity. They are colourless and have a good chemical and photochemical stability. Further, with the compounds provided by the invention there can be manufactured mixtures which have an improved melting behaviour and no smectic tendencies or only slight smectic tendencies. Although most of the compounds provided by the invention are not themselves liquid crystalline, in mixtures they generally produce no clearing point depressions or only slight clearing point depressions. They are therefore especially suitable as components of liquid crystal mixtures with negative dielectric anisotropy and as components of liquid crystal mixtures which are used in the two-frequency matrix addressing. However, they can also be used in mixtures with positive dielectric anisotropy, for example in order to adapt the threshold potential to the electro-optical cell which is used.

DETAILED DESCRIPTION OF THE INVENTION

The present invention is concerned with novel pyridazine derivatives of the formula

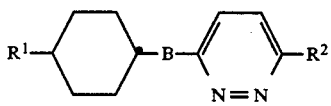

wherein B is —C≡C— or —CH$_2$CH$_2$—, R$^1$ is straight-chain C$_1$–C$_{12}$-alkyl and R$^2$ is straight-chain C$_1$–C$_{12}$-alkyl or straight-chain C$_1$–C$_{12}$-alkoxy.

The invention is also concerned with the manufacture of the compounds of the formula I above, liquid crystalline mixtures which contain these compounds as well as their use in electro-optical devices.

It has now been found that the compounds provided by the invention have a dielectric anisotropy of about −9, a good solubility in known liquid crystal mixtures and a low viscosity. They are colourless and have a good chemical and photochemical stability. Further, with the compounds provided by the invention there can be manufactured mixtures which have an improved melting behaviour and no smectic tendencies or only slight smectic tendencies. Although most of the compounds provided by the invention are not themselves liquid crystalline, in mixtures they generally produce no clearing point depressions or only slight clearing point depressions. They are therefore especially suitable as components of liquid crystal mixtures with negative dielectric anisotropy and as components of liquid crystal mixtures which are used in the two-frequency matrix addressing. However, they can also be used in mixtures with positive dielectric anisotropy, for example in order to adapt the threshold potential to the electro-optical cell which is used.

In the scope of the present invention, the terms "straight-chain alkyl" or "straight-chain C$_1$–C$_{12}$-alkyl" signify the groups methyl, ethyl, propyl, butyl, pentyl, hexyl, heptyl, octyl, nonyl, decyl, undecyl and dodecyl and the term "straight-chain C$_1$–C$_{12}$-alkoxy" signifies the groups methoxy, ethoxy, propoxy, butoxy, pentyloxy, hexyloxy, heptyloxy, octyloxy, nonyloxy, decyloxy, undecyloxy and dodecyloxy.

The term "alkali metal" denotes sodium, potassium or lithium.

The term "halogen" denotes fluorine, chlorine or bromine.

Depending on the significance or group B, formula I above embraces compounds of the following formulae

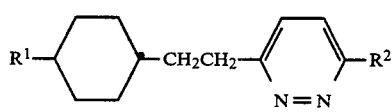

and

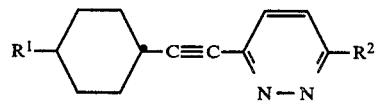

wherein R$^1$ and R$^2$ have the significance given earlier.

R$^2$ in formulae I, Ia and Ib above preferably represents straight-chain C$_1$–C$_{12}$-alkyl. Preferred groups denoted by R$^1$ are the straight-chain C$_3$–C$_7$-alkyl groups. Preferred alkyl and alkoxy groups denoted by R$^2$ are straight-chain C$_1$–C$_7$-alkyl groups (especially straight-chain C$_2$–C$_7$-alkyl groups) and straight-chain C$_1$–C$_6$-alkoxy groups.

Examples of preferred compounds provided by the invention are the compounds of formula I in which R$^1$, B and R$^2$ have the significances given in Table 1 as well as the compounds of formula I named in the Examples hereinafter.

TABLE 1

| R$^1$ | B | R$^2$ |
| --- | --- | --- |
| C$_5$H$_{11}$ | —CH$_2$CH$_2$— | C$_2$H$_5$ |
| C$_7$H$_{15}$ | —CH$_2$CH$_2$— | C$_2$H$_5$ |
| C$_4$H$_9$ | —CH$_2$CH$_2$— | C$_3$H$_7$ |
| C$_5$H$_{11}$ | —CH$_2$CH$_2$— | C$_3$H$_7$ |
| C$_7$H$_{15}$ | —CH$_2$CH$_2$— | C$_3$H$_7$ |
| C$_3$H$_7$ | —CH$_2$CH$_2$— | C$_5$H$_{11}$ |
| C$_4$H$_9$ | —CH$_2$CH$_2$— | C$_5$H$_{11}$ |
| C$_5$H$_{11}$ | —CH$_2$CH$_2$— | C$_5$H$_{11}$ |
| C$_3$H$_7$ | —CH$_2$CH$_2$— | C$_7$H$_{15}$ |
| C$_5$H$_{11}$ | —CH$_2$CH$_2$— | OC$_2$H$_5$ |
| C$_7$H$_{15}$ | —CH$_2$CH$_2$— | OC$_2$H$_5$ |
| C$_3$H$_7$ | —CH$_2$CH$_2$— | OC$_4$H$_9$ |
| C$_4$H$_9$ | —CH$_2$CH$_2$— | OC$_4$H$_9$ |
| C$_5$H$_{11}$ | —CH$_2$CH$_2$— | OC$_4$H$_9$ |
| C$_3$H$_7$ | —CH$_2$CH$_2$— | OC$_6$H$_{13}$ |
| C$_3$H$_7$ | —C≡C— | C$_3$H$_7$ |
| C$_3$H$_7$ | —C≡C— | C$_4$H$_9$ |
| C$_3$H$_7$ | —C≡C— | C$_5$H$_{11}$ |
| C$_3$H$_7$ | —C≡C— | C$_6$H$_{13}$ |
| C$_3$H$_7$ | —C≡C— | C$_7$H$_{15}$ |
| C$_3$H$_7$ | —C≡C— | OCH$_3$ |
| C$_3$H$_7$ | —C≡C— | OC$_2$H$_5$ |
| C$_3$H$_7$ | —C≡C— | OC$_3$H$_7$ |
| C$_3$H$_7$ | —C≡C— | OC$_4$H$_9$ |
| C$_3$H$_7$ | —C≡C— | OC$_5$H$_{11}$ |
| C$_3$H$_7$ | —C≡C— | OC$_6$H$_{13}$ |
| C$_4$H$_9$ | —C≡C— | C$_3$H$_7$ |
| C$_4$H$_9$ | —C≡C— | C$_5$H$_{11}$ |
| C$_4$H$_9$ | —C≡C— | C$_7$H$_{15}$ |
| C$_4$H$_9$ | —C≡C— | OCH$_3$ |
| C$_4$H$_9$ | —C≡C— | OC$_2$H$_5$ |
| C$_4$H$_9$ | —C≡C— | OC$_3$H$_7$ |
| C$_4$H$_9$ | —C≡C— | OC$_4$H$_9$ |
| C$_5$H$_{11}$ | —C≡C— | CH$_3$ |
| C$_5$H$_{11}$ | —C≡C— | C$_2$H$_5$ |
| C$_5$H$_{11}$ | —C≡C— | C$_3$H$_7$ |
| C$_5$H$_{11}$ | —C≡C— | C$_4$H$_9$ |
| C$_5$H$_{11}$ | —C≡C— | C$_5$H$_{11}$ |
| C$_5$H$_{11}$ | —C≡C— | C$_6$H$_{13}$ |
| C$_5$H$_{11}$ | —C≡C— | C$_7$H$_{15}$ |
| C$_5$H$_{11}$ | —C≡C— | OCH$_3$ |
| C$_5$H$_{11}$ | —C≡C— | OC$_2$H$_5$ |
| C$_5$H$_{11}$ | —C≡C— | OC$_3$H$_7$ |
| C$_5$H$_{11}$ | —C≡C— | OC$_4$H$_9$ |
| C$_5$H$_{11}$ | —C≡C— | OC$_5$H$_{11}$ |
| C$_5$H$_{11}$ | —C≡C— | OC$_6$H$_{13}$ |
| C$_6$H$_{13}$ | —C≡C— | C$_3$H$_7$ |
| C$_6$H$_{13}$ | —C≡C— | C$_5$H$_{11}$ |
| C$_6$H$_{13}$ | —C≡C— | OCH$_3$ |
| C$_6$H$_{13}$ | —C≡C— | OC$_2$H$_5$ |
| C$_6$H$_{13}$ | —C≡C— | OC$_4$H$_9$ |
| C$_7$H$_{15}$ | —C≡C— | CH$_3$ |
| C$_7$H$_{15}$ | —C≡C— | C$_2$H$_5$ |
| C$_7$H$_{15}$ | —C≡C— | C$_3$H$_7$ |
| C$_7$H$_{15}$ | —C≡C— | C$_4$H$_9$ |
| C$_7$H$_{15}$ | —C≡C— | C$_5$H$_{11}$ |

TABLE 1-continued

| R¹ | B | R² |
|---|---|---|
| C₇H₁₅ | —C≡C— | OCH₃ |
| C₇H₁₅ | —C≡C— | OC₂H₅ |
| C₇H₁₅ | —C≡C— | OC₃H₇ |
| C₇H₁₅ | —C≡C— | OC₄H₉ |

The compounds of formula I can be manufactured in accordance with the invention by the following procedure:

(a) for the manufacture of the compounds of formula I in which B represents the group —C≡C—, reacting a compound of the formula

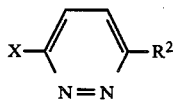
IV wherein X represent chlorine, bromine or iodine and R² has the significance given above, with a compound of the formula

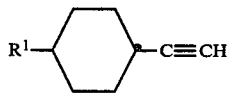
V wherein R¹ has the significance given above, in the presence of copper (I) iodide, a triphenylphosphine-palladium compound and an amine, or (b) for the manufacture of the compounds of formula I in which B represents the group —C≡C— and R² represents straight-chain $C_1$–$C_{12}$-alkoxy, reacting a compound of the formula

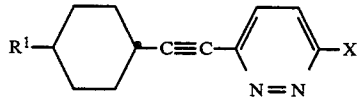
VI wherein X represents chlorine, bromine or iodine and R¹ has the significance given above, with an alkali metal alkanolate, or (c) for the manufacture of the compounds of formula I in which B represents the group —CH₂CH₂— and R² represents straight-chain $C_1$–$C_{12}$-alkyl, oxidizing a compound of the formula

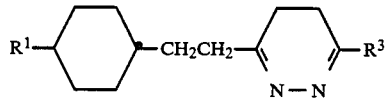
II wherein R³ represents straight-chain $C_1$–$C_{12}$-alkyl and R¹ has the significance given above, or a tautomeric dihydropyridazine, or (d) for the manufacture of the compounds of formula I in which B represents the group —CH₂CH₂— and R² represents straight-chain $C_1$–$C_{12}$-alkoxy, reacting a compound of the formula

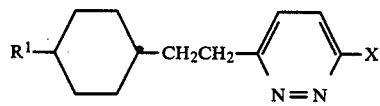
III wherein X represents chlorine, bromine or iodine and R¹ has the significance given above, with an alkali metal alkanolate, or (e) for the manufacture of the compounds of formula I in which B represents the group —CH₂CH₂—, catalytically hydrogenating a compound of formula I in which B represents the group —C≡C—.

The reaction of a compound of formula IV with a compound of formula V in the presence of copper (I) iodide, a triphenylphosphine-palladium compound and an amine (process variant a) can be carried out in a manner known per se; for example, in an analogous manner to the reactions described in Chem. Pharm. Bull, 28, 3488 (1980), Synthesis 627 (1980) and J. Org. Chem. 46, 2280 (1981). Suitable triphenylphosphine-palladium compounds are bis-(triphenylphosphine)-palladium (II) dichloride, tetrakis-(triphenylphosphine)-palladium and the like. Suitable bases are, for example, triethylamine, piperidine, diethylamine and the like. Tertiary amines are preferred. Temperature and pressure are not critical aspects in this reaction. Atmospheric pressure and a temperature between 0° C. and about 40° C. are conveniently used. X in formula IV preferably represents chlorine or bromine, especially bromine.

The reaction of a compound of formula VI or III with an alkali metal alcoholate, namely the corresponding alkali metal alkanolate, (process variants b and d) can be carried out in a manner known per se. Sodium is the preferred alkali metal. The reaction can be carried out in an inert organic solvent, for example an ether or a saturated or aromatic hydrocarbon such as diethyl ether, dioxan, benzene, toluene, hexane and the like. Preferably, however, the alcohol corresponding to the alcoholate is used as the solvent (optionally in combination with an inert organic solvent). In this case, the alcoholic solution of the alcoholate is conveniently prepared by reacting an excess of the alcohol with sodium, sodium hydride, potassium hydride and the like. Temperature and pressure are not critical aspects in the reaction. Atmospheric pressure and a temperature between room temperature and the reflux temperature of the reaction mixture, preferably about 40° C. to 60° C., are, however, conveniently used. X in formulae III and VI preferably represents chlorine or bromine.

The oxidation of a compound of formula II (process variant c) can be carried out in a manner known per se; for example, with 2,3-dichloro-5,6-dicyanobenzoquinone in dioxan, with sodium nitrite in glacial acetic acid and ethanol, with isopentyl nitrite in glacial acetic acid and the like. Temperature and pressure are not critical aspects in this reaction. However, atmospheric pressure and a temperature between room temperature and the reflux temperature are conveniently used. The compounds of formula II are, however, preferably oxidized to compounds of formula I by catalytic dehydrogenation in a manner known per se. The dehydrogenation can be carried out with any catalyst usually used in dehydrogenation reactions, examples of such catalysts being palladium, platinum and the like (optionally or an inert carrier material such as carbon). Palladium is the preferred catalyst. As the solvent there can be used any inert organic solvents such as alcohols, ethers, esters, carboxylic acids and the like, for example ethanol, dioxan, ethyl acetate or glacial acetic acid. Ethanol is the preferred solvent. Temperature and pressure are not critical aspects in this reaction. A temperature between room temperature (about 23° C.) and the reflux temperature of the reaction mixture and atmospheric pressure are conveniently used.

The compounds of formula II can rearrange to tautomeric compounds by migration of the double bonds in the dihydropyridazine ring. Such rearrangements can be brought about, for example, by the presence of a trace of acid or base. Since, however, the tautomeric dihydropyridazines can also be oxidized to compounds of formula I under the aforementioned conditions, not only a compound of formula II but also a tautomeric dihydropyridazine or a mixture of such compounds can be used in process variant (c).

The catalytic hydrogenation of a compound of formula I in which B represents the group —C≡C—, i.e. a compound of formula Ib, (process variant e) can be carried out in a manner known per se in the presence of usual hydrogenation catalysts. Preferred catalysts are palladium, platinum and the like, optionally on an inert carrier material (e.g. carbon). The hydrogenation is conveniently carried out in an inert organic solvent, for example in a saturated alcohol, ether, ester, hydrocarbon or a saturated carboxylic acid such as, for example, ethanol, dioxan, ethyl acetate, hexane, glacial acetic acid and the like. Temperature and pressure are not critical aspects in this reaction. A temperature between room temperature and the boiling point of the reaction mixture and a pressure of about 1 to 5 atmospheres are conveniently used.

The starting materials of formulae II–VI are novel and also form objects of the present invention.

The compounds of formulae II, III and V and the compounds of formula IV in which $R^2$ represents straight-chain $C_1$–$C_{12}$-alkyl can be prepared in a manner known per se; for example, according to Reaction Schemes A–D hereinafter in which $R^1$ and $R^3$ represent straight-chain $C_1$–$C_{12}$-alkyl and X represents chlorine, bromine or iodine, preferably chlorine or bromine.

Scheme A

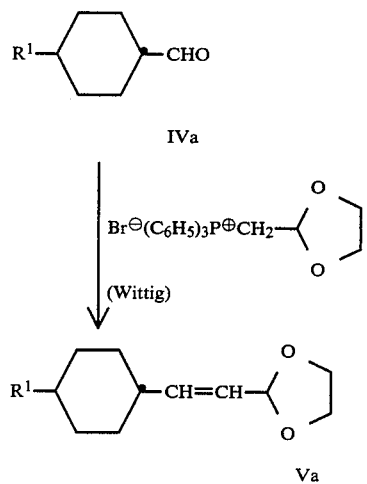

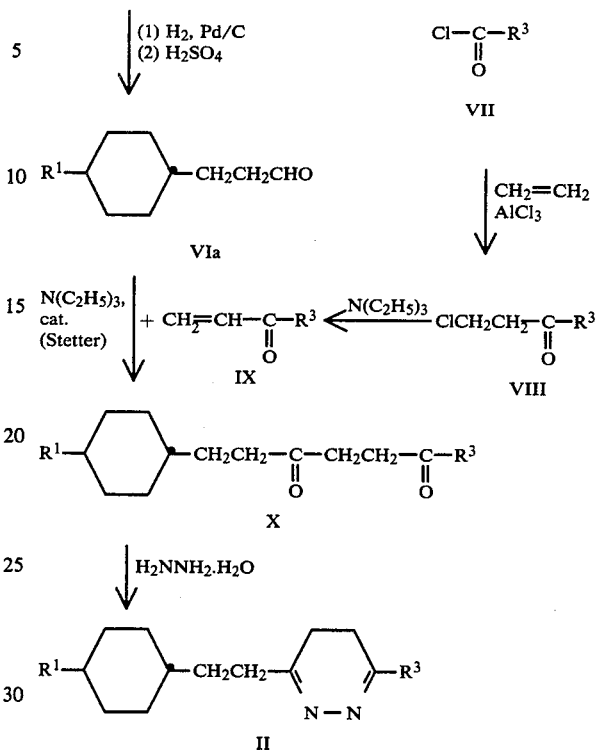

Scheme B

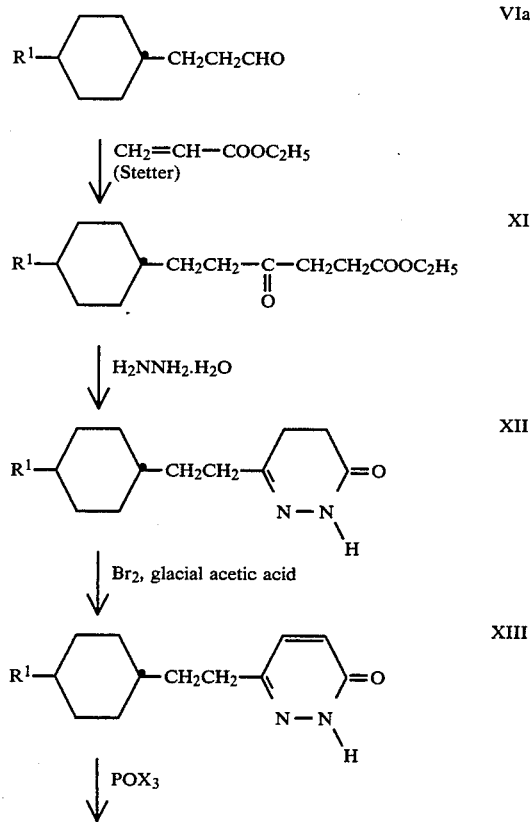

-continued
Scheme B

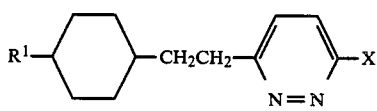

Scheme C

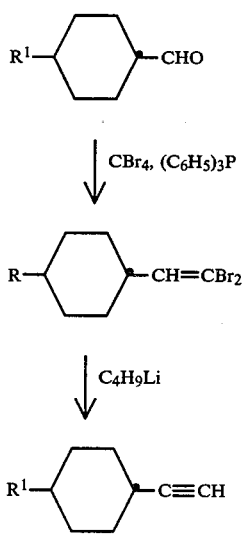

Scheme D

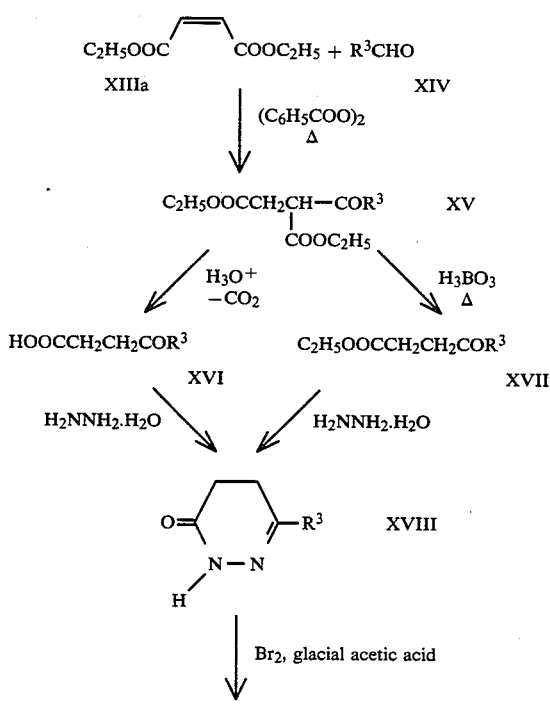

-continued
Scheme D

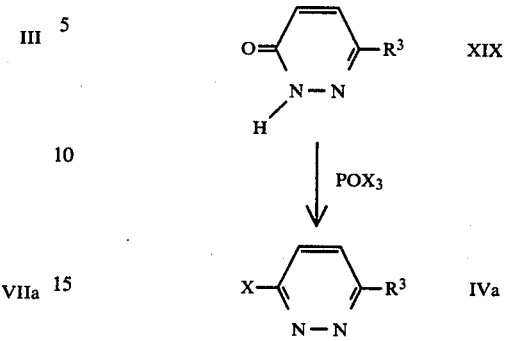

The compounds of formulae IVa and VII are known compounds or are analogues of known compounds and can be prepared according to known methods from known compounds.

The addition of an aldehyde of formula VIa to a double bond according to Scheme A or B can be carried out according to the method of Stetter [Chem. Ber. 114 (1981) 581] in the presence of a 1,3-thiazolium salt catalyst. 3-Benzyl-5-(2-hydroxyethyl)-4-methyl-1,3-thiazolium chloride is the preferred catalyst in Scheme A and 3-(2-ethoxyethyl)-5-(2-hydroxyethyl)-4-methyl-1,3-thiazolium bromide is the preferred catalyst in Scheme B.

As mentioned, the compounds of formula II can also be present in tautomeric form or as a mixture of tautomeric forms.

The compounds of formula XVII can also be obtained from ethyl acrylate and an aldehyde $R^3CHO$ according to the method described by Stetter in Chem. Ber. 113, 690 (1980).

The compounds of formulae Ib and IV in which $R^2$ represents alkoxy and the compounds of formula VI can be obtained from 3,6-dihalopyridazines (e.g. 3,6-dichloropyridazine). In this manner, pyridazines of formula I can be obtained starting from 3,6-dihalopyridazines in two steps, namely by reaction with a compound of formula V in an analogous manner to process variant (a) and by etherification with an alkali metal alcoholate in an analogous manner to process variant (b). These two steps can be carried out in optional sequence, i.e. the process can proceed via compounds of formula IV or VI.

The compounds provided by the invention can be used in the form of mixtures with a liquid crystalline carrier material. The carrier material can contain usual liquid crystal components such as, for example, substances from the classes of schiff's bases, azobenzenes, azoxybenzenes, phenyl benzoates, cyclohexanecarboxylic acid phenyl esters, cyclohexanecarboxylic acid cyclohexyl esters, biphenyls, terphenyls, phenylcyclohexanes, cyclohexylbiphenyls, phenylpyrimidines, diphenylpyrimidines, cyclohexyl-phenylpyrimidines, phenyldioxanes, phenylbicyclo[2.2.2]octanes, phenylpyridazines and the like. Such substances are known to the person skilled in the art and many of them are, moreover, commercial available. In the manufacture of the mixtures care should, however, be taken that suitable liquid crystalline compounds are used in a sufficient amount so that the total mixture has a sufficiently large mesophase range.

The mixtures provided by the invention conveniently contain about 1–50 wt.%, preferably about 3–30 wt.%, of compounds of formula I.

In principle, the compounds provided by the invention can be used in any liquid crystalline mixtures, for example even in mixtures with positive dielectric anisotropy in order to adjust the dielectric anisotropies to the cell which is used. The compounds provided by the invention are, however, preferably used in mixtures with negative dielectric anisotropy or in mixtures which are suitable for the two-frequency control. Such mixtures can be manufactured in a manner known per se.

The mixtures provided by the invention for the two-frequency matrix addressing preferably consist of three components A, B and C, each of which contains one or more compounds, with component A having a viscosity of at most 40 cp, a clearing point of at least 40° C. and a dielectric anisotropy between −2 and +1, component B having a dielectric anisotropy below −2 and containing at least one compound of formula I, and component C having a dielectric anisotropy above 30 10, a clearing point of at least 100° C. and a cross-over frequency in the total mixture of at most 15 kHz at 20° C.

Such mixtures preferably consist of at least about 30 wt.% of component A, about 3–50 wt.% of component B and about 5–40 wt.% of component C and particularly of about 30–87 wt.% of component A, about 3–40 wt.% of component B and about 10–30 wt.% of component C.

Compounds and mixtures having the above properties required for the components A, B and C are in principle known to the person skilled in the art. The total mixture must have nematic or cholesteric properties. Component A can be nematic or cholesteric and component B can be nematic, cholesteric or, provided that the total mixture is not smectic, also smectic.

Compounds and mixtures which are suitable as component A are to a large extent known and many of them are also commercially available. Component A preferably contains one or more compounds of the following formulae

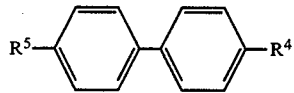  XXI

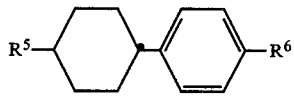  XXII

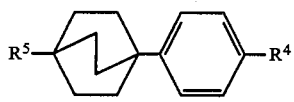  XXIII

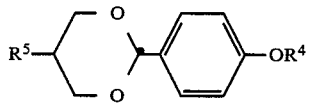  XXIV

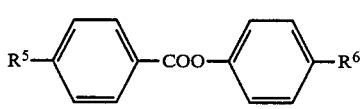  XXV

-continued

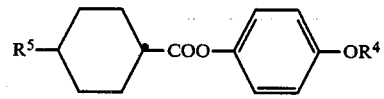  XXVI

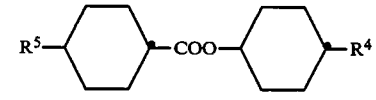  XXVII

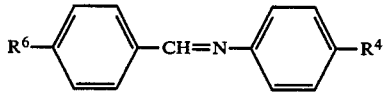  XXVIII

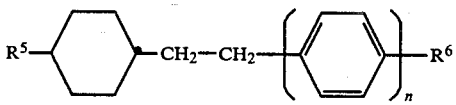  XXIX

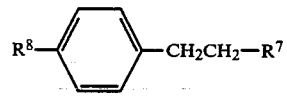  XXX

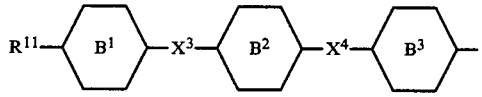  XXXI

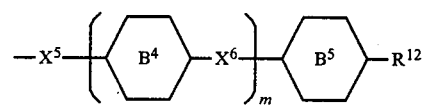

wherein $R^4$ and $R^5$ represent straight-chain $C_1$–$C_8$-alkyl, $R^6$ represents straight-chain $C_1$–$C_8$-alkyl or $C_1$–$C_8$-alkoxy and n stands for 1 or 2; $R^8$ represents trans-4-alkylcyclohexyl, 4′-alkyl-4-biphenylyl, p-(trans-4-alkylcyclohexyl)phenyl, 2-(trans-4-alkylcyclohexyl)ethyl or p-[2-(trans-4-alkylcyclohexyl)ethyl]phenyl and $R^7$ represents trans-4-alkylcyclohexyl, or $R^8$ represents trans-4-alkylcyclohexyl and $R^7$ represents p-(trans-4-alkylcyclohexyl)phenyl, p-[2-(trans-4-alkylcyclohexyl)ethyl]phenyl or 4′-(trans-4-alkylcyclohexyl)-4-biphenylyl, or $R^8$ represents p-alkylphenyl and $R^7$ represents p-[2-(trans-4-alkylcyclohexyl)ethyl]phenyl, and the alkyl groups in $R^7$ and $R^8$ are straight-chain $C_1$–$C_7$-alkyl; m stands for 0 or 1; one of the symbols $X^3$ and $X^4$ represents an ester group —COO— or —OOC— and the remainder of the symbols $X^3$, $X^4$, $X^5$ and $X^6$ represent a single covalent bond, or one of these symbols also represents the group —CH$_2$CH$_2$—; rings $B^1$ and $B^5$ represent a group of the formula

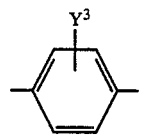  XXXII or trans-1,4-cyclohexylene; rings $B^2$, $B^3$ and $B^4$ represent a group of formula XXXII or, insofar as they are not linked with at least one of the other two or these rings by a single covalent bond, also trans-1,4-cyclohexylene; $Y^3$ reprepresents hydrogen or on a ring of formula XXXII which is not linked with a further ring via a single covalent bond also fluorine, chlorine or methyl; $R^{11}$ and $R^{12}$ represent straight-chain $C_1$–$C_7$-alkyl or on a ring of formula XXXII also straight-chain $C_1$–$C_7$-alkoxy.

The compounds of formulae XXI, XXII, XXVI, XXIX, XXX and XXXI are especially preferred.

The compounds of formula I above have been found to be especially suitable compounds for component B. Other compounds suitable for component B which can be used in admixture with one or more compounds of formula I are, for example, the phenylpyridazines and diphenylpyridazines mentioned in Z. Chemie 17, 333 (1977), J. prakt. Chemie 151, 221 (1938), Z. Chemie 6, 467 (1966) and Mol. Cryst. Liq. Cryst. 25, 299 (1974) and the compounds having two lateral cyano groups described in German Offenlegungsschriften Nos. 2 933 563 and 2 937 700. Especially suitable compounds for component B which can be used in admixture with one or more compounds of formula I are the compounds of the following formulae

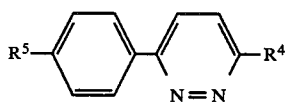  XXXIII

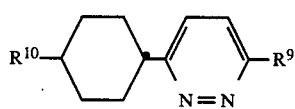  XXXIV

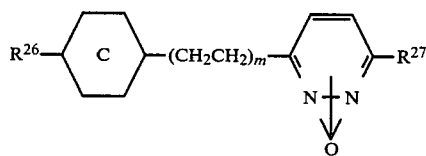  XX

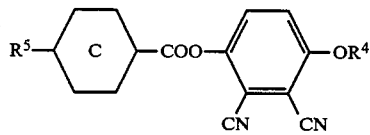  XXXV

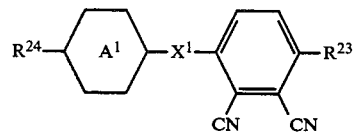  XXXVI wherein $R^4$ and $R^5$ represent straight-chain $C_1$–$C_8$-alkyl and ring C represents 1,4-phenylene or trans-1,4-cyclohexylene; $R^9$ represents straight-chain $C_1$–$C_{10}$-alkyl, $C_2$–$C_{10}$-1-alkynyl, $C_1$–$C_{10}$-alkoxy, p-($C_1$–$C_{10}$-alkyl)phenyl, p-($C_1$–$C_{10}$-alkoxy)phenyl or trans-4-($C_1$–$C_{10}$-alkyl)cyclohexyl and $R^{10}$ represents straight-chain $C_1$–$C_{12}$-alkyl; $R^{23}$ and $R^{24}$ represent straight-chain $C_1$–$C_{12}$-alkyl or on an aromatic ring also straight-chain $C_1$–$C_{12}$-alkoxy, or one of $R^{23}$ and $R^{24}$ also represents a group of the formula

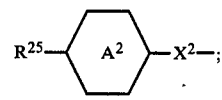  XXXVII $X^1$ and $X^2$ represent single covalent bonds or one of $X^1$ and $X^2$ also represents —$CH_2CH_2$—; rings $A^1$ and $A^2$ represent 1,4-phenylene or, insofar as $X^1$ or $X^2$ represents —$CH_2CH_2$—, also trans-1,4-cyclohexylene; and $R^{25}$ represents straight-chain $C_1$–$C_{12}$-alkyl or on an aromatic ring $A^2$ also straight-chain $C_1$–$C_{12}$-alkoxy; m stands for 0 or 1; $R^{26}$ represents $C_1$–$C_{12}$-alkyl or, insofar as ring C represents 1,4-phenylene, also $C_1$–$C_{12}$-alkoxy and $R^{27}$ represents $C_1$–$C_{12}$-alkyl, $C_1$–$C_{12}$-alkoxy or $C_2$–$C_{12}$-1-alkynyl; and the alkyl, alkoxy and 1-alkynyl groups in $R^9$, $R^{26}$ and $R^{27}$ are straight-chain groups.

The compounds of formulae XXXIV and XXXVI are especially preferred.

Suitable compounds for component C are, for example, the compounds having three or four 1,4-phenylene or trans-1,4-cyclohexylene groups, a polar end group and optionally a lateral halogen or cyano substituent which are described in Mol. Cryst. Liq. Cryst. 63, 129 (1981) and German Offenlegungsschriften Nos. 2 736 772, 2 752 975 and 3 046 872. Especially suitable compounds for component C are, however, the compounds of the formula

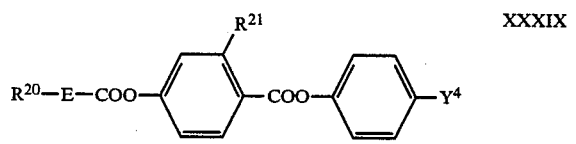  XXXVIII wherein $X^8$ represents a single covalent bond or the ester group —COO—; $X^7$ represents a single covalent bond, the ester group —COO—, the ethylene group —$CH_2CH_2$— or, insofar as $X^8$ represents the ester group —COO—, also 1,4-phenylene; ring $A^3$ represents a benzene ring or trans-1,4-cyclohexylene; ring $A^4$ represents a benzene ring or, insofar as $X^8$ represents the ester group —COO— and $X^7$ represents a single covalent bond, the ester group —COO— or the ethylene group —$CH_2CH_2$—, also trans-1,4-cyclohexylene; the symbols $Z^1$, $Z^2$ and $Z^3$ represent hydrogen or on a benzene ring which is not linked directly with a further ring via a single covalent bond also halogen, cyano or methyl; $Y^2$ represents cyano, nitro, 2,2-dicyanovinyl or, insofar as $Y^1$ represents hydrogen, also 2,2-dicyano-1-methylvinyl; $Y^1$ represents halogen, cyano, $C_1$–$C_3$-alkyl or, insofar as $X^7$ represents p-phenylene or $Y^2$ represents nitro or $Z^1$ and/or $Z^2$ are/is different from hydrogen, also hydrogen; and $R^{19}$ represents $C_1$–$C_{12}$-alkyl or on a benzene ring also $C_1$–$C_{12}$-alkoxy, and the compounds of the formula

XXXIX wherein $R^{21}$ represents hydrogen, fluorine, chlorine, bromine or the cyano group, $Y^4$ represents 2,2-dicyanovinyl, 2,2-dicyano-1-methylvinyl or cyano, $R^{20}$ and E together represent p-$R^{20}$-phenyl, trans-4-$R^{20}$- cyclohexyl, 4'-R$^{20}$-4-biphenylyl, p-(trans-4-R$^{20}$-cyclohexyl)phenyl, p-(5-R$^{20}$-2-pyrimidinyl)phenyl, p-[2-(p'-R$^{20}$-phenyl)ethyl]phenyl, p-[2-(trans-4-R$^{20}$-cyclohexyl)ethyl]phenyl, trans-4-[2-(p-R$^{20}$-phenyl)ethyl]cyclohexyl or trans-4-[2-(trans-4-R$^{20}$-cyclohexyl)ethyl]cyclohexyl, and R$^{20}$ represents straight-chain $C_1$-$C_{12}$-alkyl or on a benzene ring also straight-chain $C_1$-$C_{12}$-alkoxy.

These compounds have large nematic mesophase ranges, low cross-over frequencies and large absolute dielectric anisotropies. The term "halogen" above stands for fluorine, chlorine or bromine. The lateral substituents $Z^1$, $Z^2$, $Z^3$ and $R^{21}$ preferably represent hydrogen or chlorine.

The mixtures provided by the invention with negative dielectric anisotropy conveniently consist of a liquid crystalline carrier material with a dielectric anisotropy of at most about +1 and at least one compound of formula I. Suitable carrier materials are to a large extent known and contain one or more compounds with negative or small positive anisotropy of the dielectric constants (compounds with positive dielectric anisotropy should in the use discussed herein be used in accordance with definition only in amounts which do not leave the anisotropy of the total mixture positive). Examples of especially preferred compounds are the compounds named above in connection with components A and B and especially the compounds of formulae XXI, XXII, XXVI, XXIX, XXX, XXXI, XXXIV, XXXV and XXXVI.

The mixtures provided by the invention can also contain optically active compounds (e.g. optically active biphenyls) and/or dichroic colouring substances (e.g. azo, azoxy or anthraquinone colouring substances), in the case of the mixtures for the two-frequency addressing as ingredients of components A, B and C depending on properties and in the case of the mixtures with negative dielectric anisotropy as ingredients of the carrier material. The amount of such compounds is determined by the solubility, the desired pitch, colour, extinction and the like. Preferably, the amount of optically active compounds amounts to at most about 4 wt.% and the amount of dichroic colouring substance amounts to at most about 10 wt.%, these percentages being based on the total mixture.

The manufacture of the liquid crystalline mixtures provided by the invention can be carried out in a manner known per se; for example, by heating a mixture of the ingredients to a temperature barely above the clearing point and subsequently cooling down.

The manufacture of an electro-optical device containing a mixture provided by the invention can also be carried out in a manner known per se; for example, by evacuating a suitable cell and introducing the mixture into the evacuated cell.

The compounds of formula XXX are novel. They can be prepared as illustrated in the following Reaction Schemes 1 and 2 in which R$^{15}$ represents trans-4-alkylcyclohexyl, 4'-alkyl-4-biphenylyl, p-(trans-4-alkylcyclohexyl)phenyl or 2-(trans-4-alkylcyclohexyl)ethyl and R$^{16}$ represents trans-4-alkylcyclohexyl, or R$^{15}$ represents trans-4-alkylcyclohexyl and R$^{16}$ represents p-(trans-4-alkylcyclohexyl)-phenyl, p-[2-(trans-4-alkylcyclohexyl)ethyl]phenyl or 4'-(trans-4-alkylcyclohexyl)-4-biphenylyl, or R$^{15}$ represents p-alkylphenyl and R$^{16}$ represents p-[2-(trans-4-alkylcyclohexyl)ethyl]phenyl and R$^{13}$ and R$^{14}$ as well as the alkyl groups in the substituents R$^{15}$ and R$^{16}$ are straight-chain $C_1$-$C_7$-alkyl.

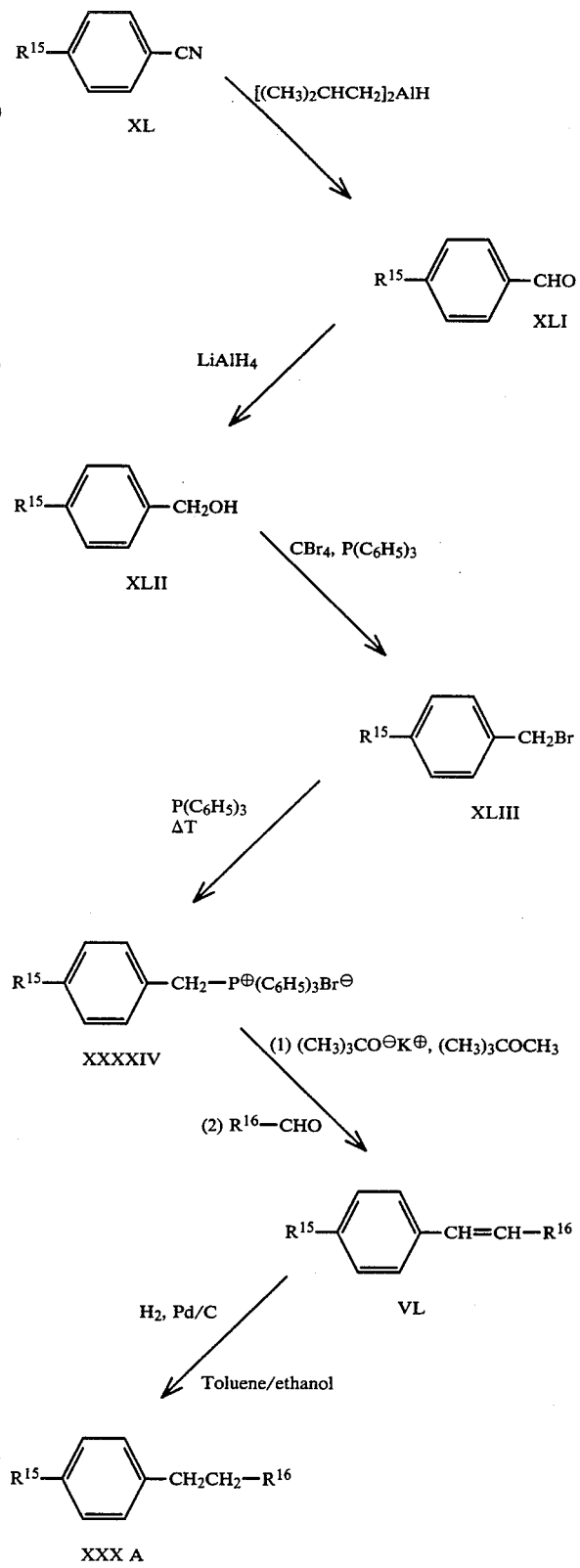

Scheme 1

Scheme 2

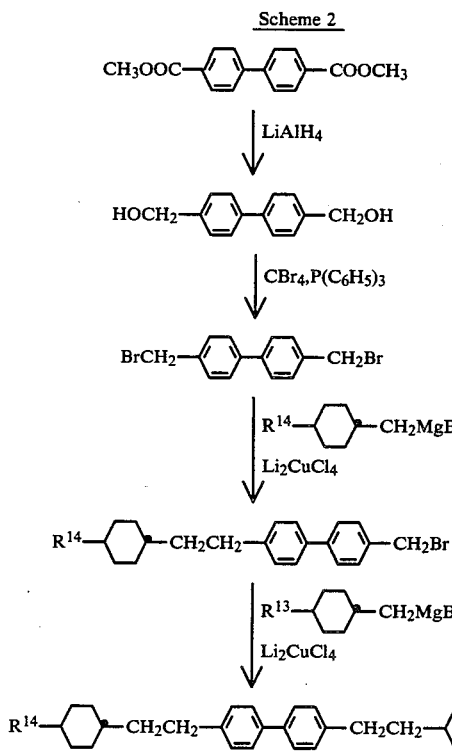

The compounds of formula R¹⁶-CHO in Scheme 1 can be obtained in a simple manner from known compounds; for example, the trans-4-alkylcyclohexanecarboxaldehydes can be obtained by Rosenmund reduction of the corresponding acid chlorides and the remaining compounds can be obtained by reducing the corresponding cyano compounds.

By reacting the compound of formula VLIII with Grignard reagents in accordance with Scheme 2 there can be obtained compounds of formula IL or directly compounds of formula XXXB in which $R^{13}$ and $R^{14}$ have the same significance. When at least about 2 mol of Grignard reagent are used per mol of the compound of formula VLIII there is generally predominantly formed directly a compound of formula XXXB.

The esters of formula XXXI are also novel. They can be obtained according to esterification methods known per se (e.g. in an analogous manner to the preparation of the compounds of formula XXXVIII described below). The starting materials required for the preparation of the esters of formula XXXI are known or are analogues of known compounds and can be prepared according to known methods.

The compounds of formula XXXIV are also novel. They can be prepared in a manner known per se by (a) for the preparation of the compounds of formula XXXIV in which $R^9$ represents an alkyl, p-alkylphenyl, p-alkoxyphenyl or trans-4-alkylcyclohexyl group, subjecting a compound of the formula

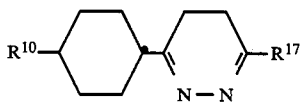

wherein $R^{17}$ represents an alkyl, p-alkylphenyl, p-alkoxyphenyl or trans-4-alkylcyclohexyl group, the alkyl and alkoxy groups in $R^{17}$ are straight-chain groups containing 1 to 10 carbon atoms and $R^{10}$ has the significance given above, or a tautomeric dihydropyridazine to oxidation (e.g. with 2,3-dichloro-5,6-dicyano-p-benzoquinone in dioxan, with sodium nitrite in glacial acetic acid and ethanol, with isopentyl nitrite in glacial acetic acid or preferably by catalytic dehydrogenation with palladium, platinium and the like), or (b) for the preparation of the compounds of formula XXXIV in which $R^9$ represents an alkoxy group, reacting a compound of the formula

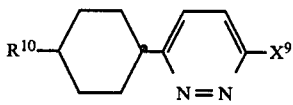

wherein $X^9$ represents chlorine or bromine and $R^{10}$ has the significance given above, with an alkali metal alcoholate (e.g. a sodium alkanolate), or (c) for the preparation of the compounds of formula XXXIV in which $R^9$ represents the ethynyl group, reacting a compound of the formula

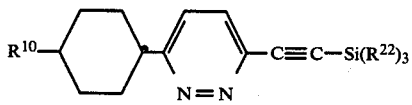

wherein $R^{22}$ represents an alkyl group containing 1 to 5 carbon atoms and $R^{10}$ has the significance given above, with a base (e.g. potassium hydroxide, sodium hydroxide or butyl lithium), or (d) for the preparation of the compounds of formula XXXIV in which $R^9$ represents a 1-alkynyl group containing 3 to 10 carbon atoms, converting a compound of the formula

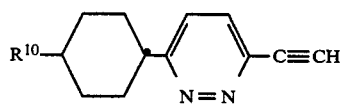

wherein $R^{10}$ has the significance given above, with a base (e.g. butyl lithium, methyl lithium, sodium amide or lithium diisopropylamide) into the corresponding ethynylide and alkylating the ethynylide with an alkyl bromide or alkyl iodide.

The compounds of formula L can rearrange to tautomeric compounds by migration of the double bonds in the dihydropyridazine ring. Such rearrangements can be brought about, for example, by the presence of a trace of acid or base. Since the tautomeric dihydropyridazines can, however, also be oxidized under the above conditions to compounds of formula XXXIV, not only a compound of formula L but also a tautomeric dihydropyridazine or a mixture of such compounds can be reacted in accordance with variant (a).

The starting materials of formulae L and LI are novel. They can be prepared as illustrated in the following Reaction Schemes 3-6 in which $R^{10}$, $R^{17}$ and $X^9$ have the significances given above and $R^{18}$ represents a straight-chain alkyl or alkoxy group containing 1 to 10 carbon atoms.

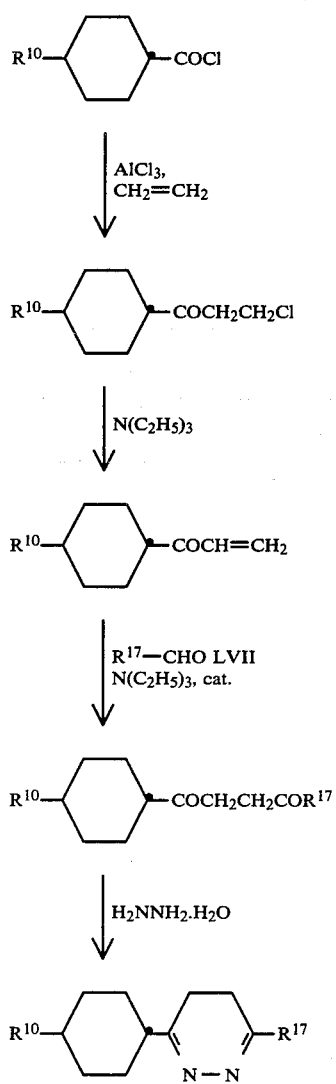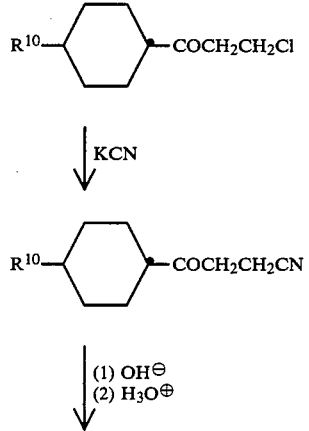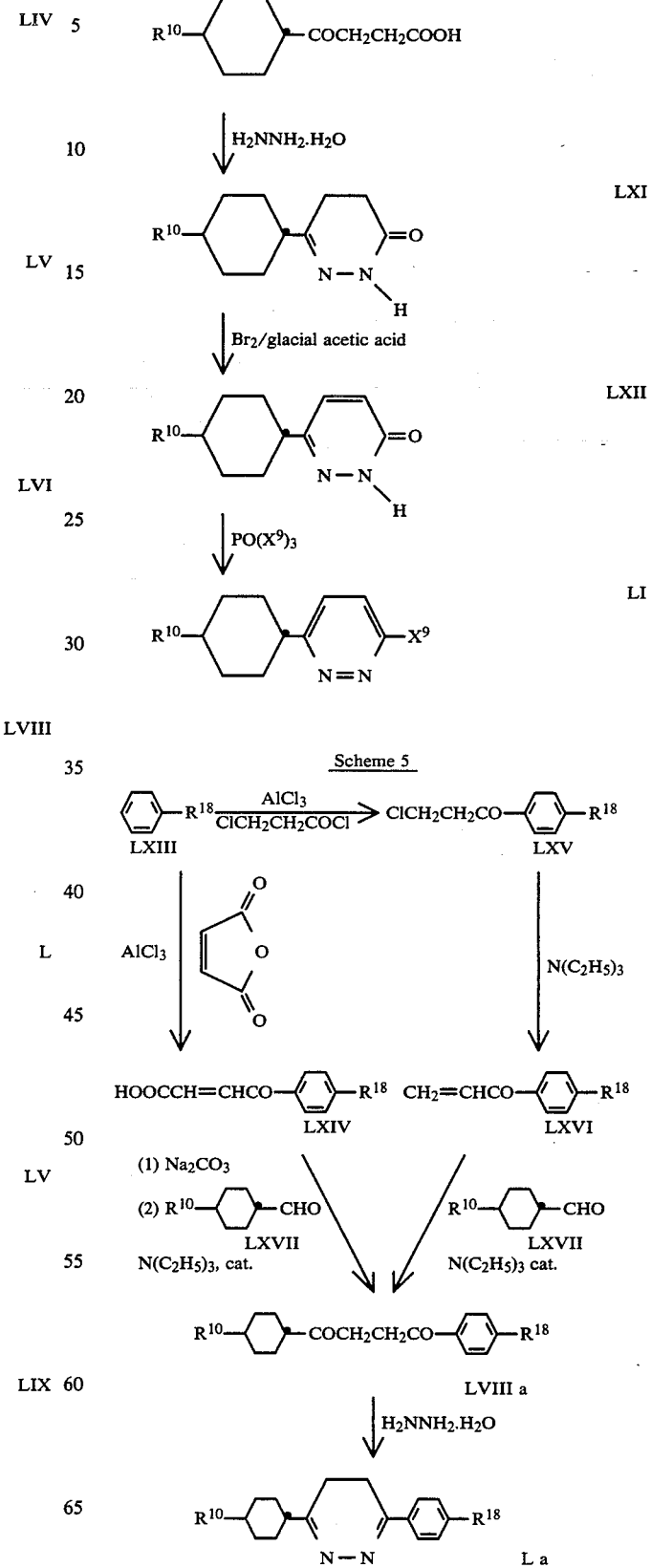

Scheme 6

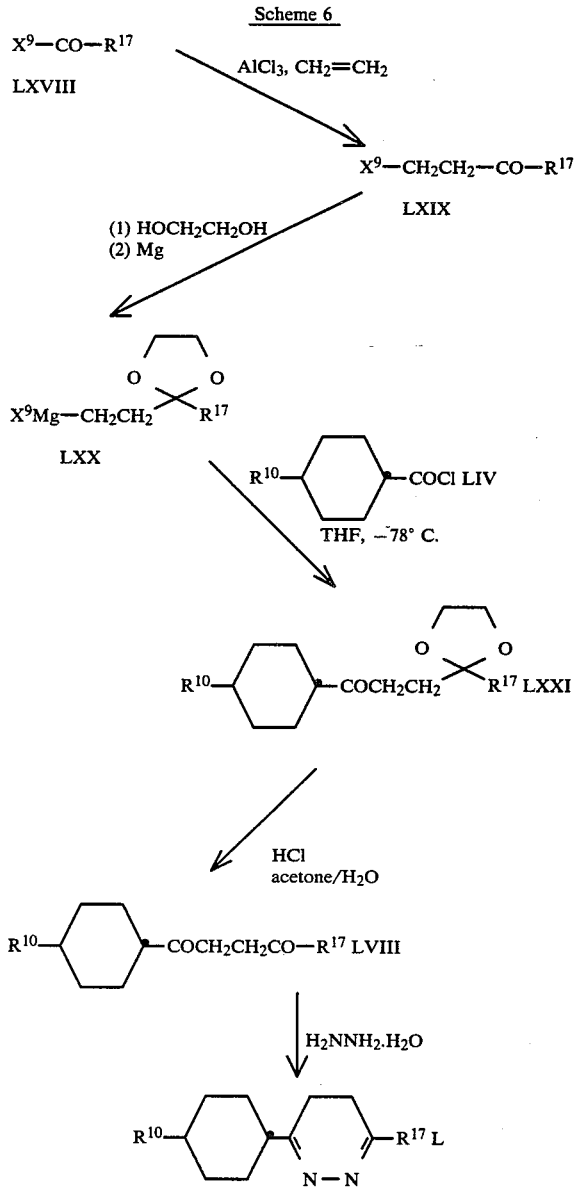

The starting materials of formulae LIV, LVII, LXIII, LXVII and LXVIII are known or are analogues of known compounds and can be prepared from known compounds in a known manner. For example, the aldehydes of formula LXVII can be prepared by Rosenmund reduction of the acid chlorides of formula LIV.

The addition of an aldehyde to a compound of formula LVI, LXIV or LXVI can be carried out according to the method of Stetter [Chem. Ber. 114 (1981) 581] in the presence of a 1,3-thiazolium salt catalyst. 3-Benzyl-5-(2-hydroxyethyl)-4-methyl-1,3-thiazolium chloride is the preferred catalyst for the addition of an aldehyde of formula LXVII or of an aldehyde of formula LVII in which $R^{17}$ represents alkyl or trans-4-alkylcyclohexyl and 3,4-dimethyl-5-(2-hydroxyethyl)-1,3-thiazolium iodide is the preferred catalyst for the addition of an aldehyde of formula LVII in which $R^7$ represents p-alkylphenyl or p-alkoxyphenyl.

The coupling of a compound of formula LXX with a compound of LIV can be carried out according to the method described by T. Sato et al. in Bull Chem. Soc. Japan 54 (1981) 505.

The compounds of formula LII are also novel. They can be obtained in a manner known per se by reacting a compound of formula LI with an ethynyltrialkylsilane in the presence of triethylamine, bis-(triphenylphosphine)-palladium (II) dichloride and copper (I) iodide.

The compounds of formula XX are also novel. They can be prepared in a manner known per se by (a) oxidizing a compound of the formula

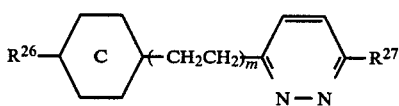

wherein m, C, $R^{26}$ and $R^{27}$ have the significances given in formula XX, with a peracid, or (b) for the preparation of the compounds of formula XX in which $R^{27}$ represents $C_2$-$C_{12}$-1-alkynyl, alkynylating a compound of the formula

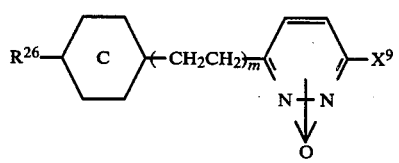

wherein $X^9$ represents chlorine or bromine and m, C and $R^{26}$ have the significances given in formula XX, the alkynylation being carried out in an analogous manner to Chem. Pharm. Bull. 28, 3488 (1980) and to process variant (a) described above for the manufacture of the compounds of formula I.

The compounds of XXXVI are also novel. They can be prepared in a manner known per se by (a) for the preparation of the compounds of formula XXXVI in which $R^{23}$ represents straight-chain $C_1$-$C_{12}$-alkyl or a group of formula XXXVII, subjecting a compound of the formula

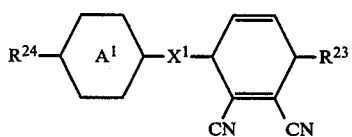

wherein $R^{23}$ represents straight-chain $C_1$-$C_{12}$-alkyl or a group of formula XXXVII and $R^{24}$, $X^1$ and ring $A^1$ have the significance given in formula XXXVI, to oxidation (e.g. with 2,3-dichloro-5,6-dicyano-p-benzoquinone in dioxan), or (b) for the preparation of the compounds of formula XXXVI in which $R^{23}$ represents straight-chain $C_1$-$C_{12}$-alkoxy, reacting a compound of the formula

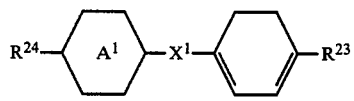

wherein $R^{23}$ represents straight-chain $C_1$-$C_{12}$-alkoxy and $R^{24}$, $X^1$ and ring $A^1$ have the significances given in formula XXXVI, with dicyanoacetylene in an ether (e.g. tetrahydrofuran) and subsequently cleaving off ethylene by heating.

The compounds of formula LXXII can be prepared, for example, by reacting an aldehyde of the formula

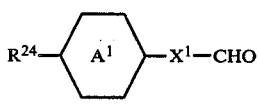

with a phosphonium salt of the formula

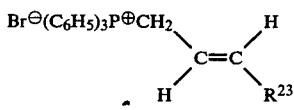

wherein $R^{23}$, $R^{24}$, $X^1$ and ring $A^1$ have the significances given in formula LXXII, in diethyl ether in the presence of butyl lithium and converting the diene obtained into a compound of formula LXXII by Diels-Alder reaction with dicyanoacetylene in tetrahydrofuran.

The compounds of formula LXXIII can be obtained, for example, by reducing a compound of the formula

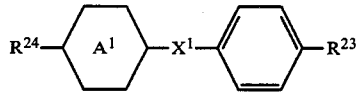

wherein $R^{23}$, $R^{24}$, $X^1$ and ring $A^1$ have the significances given in formula LXXIII, with lithium and liquid ammonia (preferably in a diethyl ether/ethanol mixture). In this case there is generally obtained the 1,4-diene or a mixture of the 1,3-diene (a compound of formula LXXIII) and the 1,4-diene. The isomerization to the 1,3-diene can be carried out, for example, with 2,3-dichloromaleic anhydride.

The compounds of formula XXXVIII are also novel. They can be prepared in a manner known per se by esterifying the acid chloride of a compound of the formula

LXXVII

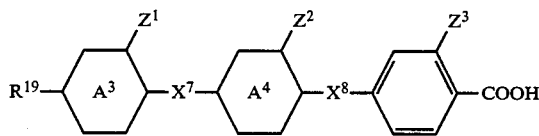

wherein $R^{19}$, $A^3$, $A^4$, $X^7$, $X^8$, $Z^1$, $Z^2$ and $Z^3$ have the significances given in formula XXXVIII, with a phenol of the formula

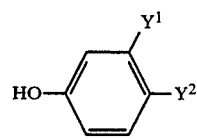

wherein $Y^1$ and $Y^2$ have the significance given in formula XXXVIII, and, if desired, reacting a compound of formula XXXVIII obtained in which $Z^1$, $Z^2$ or $Z^3$ represents bromine with copper (I) cyanide, sodium cyanide or potassium cyanide.

The compounds of formula LXXVIII in which $Y^2$ represents 2,2-dicyanovinyl can be prepared, for example, by converting 3-$Y^1$-anisole into 4-methoxy-2-$Y^1$-benzaldehyde by Vilsmeier reaction with dimethylformamide in the presence of phosphorous oxychloride, then hydrolyzing the methoxy group (e.g. by heating under reflux with pyridinium chloride and subsequent fractional distillation) and finally converting the 4-hydroxy-2-$Y^1$-benzaldehyde into the comound of formula LXXVIII in which $Y^2$ represents 2,2-dicyanovinyl by Knoevenagel condensation with malononitrile (e.g. in the presence of catalytic amounts of glacial acetic acid and sodium acetate in boiling toluene). The remaining compounds of formula LXXVIII are known or are analogues of known compounds or can be prepared from known compounds by conventional techniques.

The compounds of formula LXXVII are also known or are analogues of known compounds and can be prepared according to known methods from known compounds.

The compounds of formula LXXVII in which $R^8$ represents the ester group —COO— can be prepared, for example, by esterifying a compound of the formula

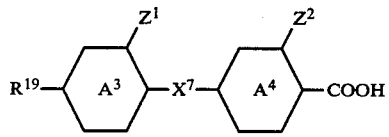

wherein $X^7$ represents a single covalent bond, the ester group —COO—, the ethylene group —CH$_2$CH$_2$— or 1,4-phenylene and $R^{19}$, $A^3$, $A^4$, $Z^1$ and $Z^2$ have the significances given in formula XXXVIII, with 4-hydroxy-2-$Z^3$-benzaldehyde in methylene chloride in the presence of dicyclohexylcarbodiimide and 4-(dimethylamino)pyridine and converting the resulting aldehyde into the corresponding acid of formula LXXVII by Jones' oxidation with chromic acid and sulphuric acid.

In the preparation of the acids of formula LXXVII in which $X^7$ represents the ethylene group —CH$_2$CH$_2$— and $X^8$ represents a single covalent bond and of the acids of formula LXXIX in which $X^7$ represents the ethylene group —CH$_2$CH$_2$—, the linkage of rings $A^3$ and $A^4$ is conveniently carried out by a Fouquet-Schlosser reaction or by a Wittig reaction. For example, 4-(bromomethyl)-2-$Z^2$-benzonitrile, 4'-(bromomethyl)-4-biphenylcarbonitrile or trans-4-(tosyloxymethyl)cyclohexanecarbonitrile can be reacted with (4-$R^{19}$-2-$Z^1$-phenyl)methylmagnesium bromide or (trans-4-$R^{19}$-cyclohexyl)methylmagnesium bromide in the presence of dilithium tetrachlorocuprate and the nitrile obtained can be hydrolyzed to the desired acid. Further, for example, 4-$R^{19}$-2-$Z^1$-benzaldehyde or trans-4-$R^{19}$-cyclohexanecarboxaldehyde can be reacted with (4-methoxycarbonyl-3-$Z^2$-phenyl)methyl-triphenylphosphonium bromide ($Z^1$ and $Z^2$ representing hydrogen, fluorine, cyano or methyl) in the presence of a base (e.g. sodium methylate), then the double bond can be catalytically hydrogenated and finally the ester group can be saponified.

The starting materials required for these reactions are known or can be prepared according to methods known per se. For example, 4-alkoxy-2-$Z^1$-acetophenone can be converted by haloform degradation into 4-alkoxy-2-

$Z^1$-benzoic acid and this can be converted into 4-alkoxy-1-(bromomethyl)-2-$Z^1$-benzene by reduction with lithium aluminium hydride and bromination (e.g. with tetrabromomethane and triphenylphosphine). From methyl 2,4-dimethylbenzoate there can be obtained, for example, by reaction with N-bromosuccinimide and subsequent isomer separation methyl 4-(bromomethyl)-2-methylbenzoate which can be converted into methyl 4-formyl-2-methylbenzoate in an analogous manner to Org. Synth. Coll. V, 825; the methyl 4-alkyl-2-methylbenzoate obtained after reaction with alkyl-triphenylphosphonium bromide and base and subsequent catalytic hydrogenation of the double bond can be saponified with sodium hydroxide to the acid or reduced with lithium aluminium hydride to the alcohol which finally can be converted with hydrogen bromide into the 4-alkyl-1-(bromomethyl)-2-methylbenzene or with manganese dioxide into the 4-alkyl-2-methylbenzaldehyde. 1-Alkyl-3-fluorobenzene can be converted, for example, into 4-alkyl-2-fluorobenzoic acid by reaction with butyl lithium and carbon dioxide and subsequent hydrolysis and 1-alkyl-3-chlorobenzene or 1-alkyl-3-bromobenzene can be converted into 4-alkyl-2-(chloro or bromo)benzoic acid by Friedel-Crafts acylation with acetyl chloride in the presence of aluminium trichloride and subsequent oxidation with sodium hypobromite; the acids obtained can then be converted with lithium aluminium hydride into the alcohols and these can be converted into the bromides with hydrogen bromide or into the aldehydes with manganese dioxide. Further, for example, 4-methyl-2-$Z^1$-benzoic acid can be reacted in sequence with thionyl chloride, ammonia and benzenesulphonyl chloride and the 4-methyl-2-$Z^1$-benzonitrile obtained can be converted into 4-(bromomethyl)-2-$Z^1$-benzonitrile with N-bromosuccinimide.

The compounds of formula XXXIX are in part also novel compounds. They can be prepared by esterification in an analogous manner to the compounds of formula XXXVIII. The acids required for the preparation of the compounds of formula XXXIX can be obtained as illustrated in Reaction Scheme 7 in which $R^{20}$, $R^{21}$ and E have the significances given in formula XXXIX above.

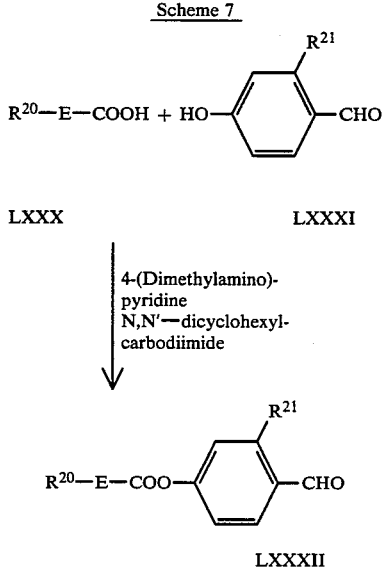

The compounds of formulae LXXX and LXXXI are known or can be prepared according to methods known per se.

The invention is also concerned with all novel compounds, mixtures, processes, uses and devices as herein described.

The manufacture of the compounds of formula I is illustrated in more detail by the following Examples. C signifies a crystalline phase, S signifies a smectic phase, N signifies a nematic phase and I signifies the isotropic phase. Unless otherwise stated, percentages and ratios relating to solvent mixtures are expressed in volume, purity data determined by gas chromatography are expressed in area % and the remaining percentages and ratios are expressed in weight, temperatures are in degrees Celsius (°C), normal pressure is about 1 atmosphere and room temperature is about 23° C. The petroleum ether is a well known mixture of low-boiling hydrocarbons. Examples 2–9 were carried out as written.

EXAMPLE 1

0.51 g of sodium is placed in a sulphonation flask under nitrogen gasification and then 13 ml of dry butanol are slowly added dropwise to that the alcohol boils slightly (hydrogen evolution). The mixture is then heated to 60° C. until the sodium has dissolved completely. After cooling to 30° C., a solution of 5.6 g of 3-chloro-6-[2-(trans-4-butylcyclohexyl)ethyl]pyridazine in 40 ml of dry butanol is added dropwise within 15 minutes. The mixture is subsequently stirred at 60° C. for a further 4 hours, cooled to room temperature and the solvent is removed on a rotary evaporator. The residue is taken up in 100 ml of hexane and washed neutral three times with 100 ml of water each time. The aqueous phases are back-extracted with 100 ml of hexane. The organic phases are dried over sodium sulphate and freed from solvent on a rotary evaporator. The crude product is chromatographed on aluminium oxide (neutral) with hexane/ethyl acetate and then recrystallized several times from ethyl acetate and hexane. There is thus obtained pure 3-butoxy-6-[2-(trans-4-butylcyclohexyl)-ethyl]pyridazine.

The 3-chloro-6-[2-(trans-4-butylcyclohexyl)ethyl]-pyridazine required as the starting material can be prepared as follows:

(a) 33.6 g of trans-4-butylcyclohexanecarboxaldehye and 128.8 g of 1,3-dioxolan-2-yl-methyl-triphenylphosphonium bromide are dissolved in 800 ml of dry N,N-dimethylformamide under nitrogen gasification, heated to 80°–90° C. and treated dropwise at this temperature within 3 hours with a freshly prepared solution of 2.1 g of lithium in 300 ml of dry methanol. The mixture is stirred at 80°–90° C. for a further 5 hours, then cooled to room temperature and concentrated on a rotary evaporator. The residue is diluted with 800 ml of methylene chloride and washed twice with 400 ml of water each time. The aqueous phases are back-extracted with 100 ml of methylene chloride. The combined organic phases are dried over sodium sulphate and concentrated. In order to remove the triphenylphosphine oxide, the resulting crude product of trans-4-butyl-1-[2-(1,3-dioxolan-2-yl)vinyl]cyclohexane is chromatographed on silica gel with methylene chloride/hexane and the solvent is then removed.

(b) The crude trans-4-butyl-1-[2-(1,3-dioxolan-2-yl)-vinyl]cyclohexane obtained is dissolved in 500 ml of ethanol, treated with 1 ml of triethylamine and 1 g of palladium/carbon (5%) and hydrogenated while shaking. After completion of the hydrogen uptake, the mixture is filtered and the residue is rinsed with 100 ml of ethanol. The filtrate is concentrated to half volume on a rotary evaporator, treated with 300 ml of water and 5 ml of concentrated sulphuric acid and heated to 80° C. for 30 minutes. For the working-up, the mixture is diluted with water, neutralized with sodium hydrogen carbonate and extracted twice with 250 ml of tert.butyl methyl ether each time. The organic phases are dried over sodium sulphate and freed from solvent on a rotary evaporator. The crude product of 3-(trans-4-butylcyclohexyl)propanal obtained is distilled in a high vacuum.

(c) 7.5 g of ethyl acrylate are dissolved in 100 ml of dry dioxan under nitrogen gasification, treated with 6.1 g of triethylamine and 1.4 g of 3-(2-ethoxyethyl)-5-(2-hydroxyethyl)-4-methyl-1,3-thiazolium bromide and heated to 80° C. A solution of 19.6 g of 3-(trans-4-butylcyclohexyl)propanal and 7.5 g of ethyl acrylate in 50 ml of dioxan is added dropwise within 5 hours. The mixture is stirred at 80° C. for a further 15 hours, then cooled to room temperature and freed from solvent on a rotary evaporator. The residue is taken up in 200 ml of tert.butyl methyl ether and washed successively with dilute sulphuric acid, dilute sodium hydrogen carbonate solution and water. The aqueous phases are back-extracted with 100 ml of tert.butyl methyl ether. The combined organic phases are dried over sodium sulphate and freed from solvent on a rotary evaporator. The crude product of ethyl 6-(trans-4-butylcyclohexyl)-4-oxo-caproate obtained is recrystallized from ethyl acetate.

(d) 29.65 g of ethyl 6-(trans-4-butylcyclohexyl)-4-oxo-caproate are dissolved in 300 ml of methanol, treated dropwise within 10 minutes with 5.5 g of hydrazine hydrate and then boiled at reflux for 2 hours. The mixture is subsequently cooled to room temperature and freed from solvent on a rotary evaporator. The residue of 6-[2-(trans-4-butylcyclohexyl)ethyl]-4,5-dihydro-3(2H)-pyridazinone is evaporated to dryness twice with 150 ml of toluene each time and subsequently dried at 40° C. in vacuo.

(e) 26.4 g of 6-[2-(trans-4-butylcyclohexyl)ethyl]-4,5-dihydro-3(2H)-pyridazinone are dissolved in 75 ml of glacial acetic acid, warmed to 40° C. and then treated dropwise with 19.2 g of bromine within 30 minutes without additional warming (exothermic). The mixture is subsequently stirred at 60° C. for a further 2 hours, cooled to room temperature, diluted with 100 ml of ethyl acetate and suction filtered. The material on the suction filter is rinsed with ethyl acetate, suspended in 200 ml of water, neutralized at 50° C. with sodium hydrogen carbonate, cooled to 0° C., suction filtered and the residue is washed with cold water. The still moist, well pressed-out crystals of 6-[2-(trans-4-butylcyclohexyl)ethyl]-3(2H)-pyridazinone are finally recrystallized from ethanol.

(f) 21.0 g of 6-[2-(trans-4-butylcyclohexyl)ethyl]-3(2H)-pyridazinone are treated with 20 ml of phosphorus oxychloride and slowly heated to reflux. After boiling under reflux for 20 minutes, the excess phosphorus oxychloride is distilled off. The residue is cooled 0° C., hydrolyzed cautiously with 100 g of crushed ice, then neutralized with sodium hydrogen carbonate and extracted three times with 100 ml of tert.butyl methyl ether each time. The combined organic phases are dried over sodium sulphate and freed from solvent on a rotary evaporator. The crude product of 3-chloro-6-[2-(trans-4-butylcyclohexyl)ethyl]pyridazine obtained is recrystallized from ethanol.

EXAMPLE 2

(a) A solution, cooled to 0° C., of 90.9 g of tetrabromomethane in 100 ml of methylene chloride was treated under argon gasification within 20 minutes with a solution of 143.9 g of triphenylphosphine in 200 ml of methylene chloride. The clear orange solution was stirred at 0° C. for a further 5 minutes and then treated dropwise within 10 minutes at 0° C. with a solution of 25 g of trans-4-pentylcyclohexanecarboxaldehyde (purity about 82%) in 80 ml of methylene chloride. After stirring at 0° C. for 30 minutes, the mixture was poured into 2.5 l of hexane and the precipitate which separated was filtered off. The filtrate was concentrated, digested with 1 l of hexane, filtered and again concentrated. Low-pressure chromatography (0.5 bar) of the residue (52.7 g) on silica gel with hexane gave 35.9 g (77.4%) of trans-1-(2,2-dibromovinyl)-4-pentylcyclohexane as a colourless oil; Rf-value (hexane) 0.58.

(b) A solution of 35.9 g of trans-1-(2,2-dibromovinyl)-4-pentylcyclohexane in 300 ml of absolute tetrahydrofuran at −70° C. was placed under argon gasification and treated within 20 minutes with 222 ml of a 1.2M solution of butyl lithium in hexane. The mixture was subsequently stirred at −70° C. for a further 2 hours, then poured into 1.2 l of water and extracted three times with 400 ml of hexane each time. The organic phases were washed twice with 400 ml of water each time, dried over magnesium sulphate and concentrated. Crystallization of the residue (19.4 g) from 250 ml of methanol at −78° C. gave 10.0 g of trans-1-ethynyl-4-pentylcyclohexane which was a colourless liquid at room temperature. Crystallization of the mother liquor, concentrated to about 100 ml, at −78° C. gave a further 3.9 g of trans-1-ethynyl-4-pentylcyclohexane. The combined batches of product were crystallized again from 300 ml of methanol at −78° C. and subsequently distilled (110° C./0.3 Torr), there being obtained 10.43 g (55%) of trans-1-ethynyl-4-pentylcyclohexane (purity 99.4%) as a colourless liquid; Rf-value (hexane) 0.41.

EXAMPLE 3

8.0 g of 3-bromo-6-propylpyridazine were dissolved in 50 ml of triethylamine in a sulphonation flask under nitrogen. The solution was cooled to 0° C., treated with 562 mg of bis-(triphenylphosphine)-palladium (II) dichloride and 76 mg of copper (I) iodide and then treated dropwise within 20 minutes with 7.5 g of trans-1-ethynyl-4-pentylcyclohexane (prepared according to Example 2). The mixture was subsequently stirred overnight while cooling with an ice-bath and then heated to 50° C. for a further 3 hours. The mixture was concentrated on a rotary evaporator. The residue was taken up in 100 ml of hexane and washed with 100 ml of water, whereby the pH value of the aqueous phase was made neutral with ammonium chloride. The aqueous phase was back-extracted twice with 50 ml of hexane each time. The combined organic phases were washed with 100 ml of water and the aqueous phase was back-extracted with 50 ml of hexane. The organic phases were dried over sodium sulphate and freed from solvent on a rotary evaporator. Chromatography of the resulting brown crystallizing oil on silica gel with hexane/ethyl acetate (vol. 2:1) gave a fraction of the desired product 3-[2-(trans-4-pentylcyclohexyl)ethynyl]-6-propylpyridazine (5.2 g) as well as a mixed fraction (4.8 g) consisting of 3-bromo-6-propylpyridazine and product. The pure fraction was recrystallized from 15 ml of ethanol at −20° C. There were thus obtained 4.0 g of white crystals which were recrystallized from 25 ml of pentane at −20° C. The crystals were subsequently dried for 2 hours in a vacuum drying oven at 40° C. and then overnight at room temperature with a slight stream of nitrogen in a high vacuum, there being obtained 3.4 g of 3-[2-(trans-4-pentylcyclohexyl)ethynyl]-6-propylpyridazine as white crystals of melting point (C-I) 118°–118.5° C.

The 3-bromo-6-propylpyridazine used as the starting material was prepared as follows:

(a) A mixture of 86 g of diethyl maleate, 144 g of butyraldehyde and 4 g of dibenzoyl peroxide was boiled at reflux for 20 hours. After completion of the reaction, the excess butyraldehyde was firstly distilled off over a Vigreux column and then the yellow coloured crude product was taken up in 250 ml of hexane and washed with 200 ml of 5% (wt./vol.) sodium hydrogen carbonate solution and 200 ml of water. The aqueous phases were back-extracted with a small amount of hexane. The combined organic phases were dried over sodium sulphate and freed from solvent on a rotary evaporator. Distillation of the resulting crude product in a high vacuum over a Vigreux column gave 104.5 g (85.6%) of diethyl 2-butyrylsuccinate as a slightly yellow coloured liquid; b.p. 84°–90° C./0.08 Torr.

(b) 92.8 g of diethyl 2-butyrylsuccinate and 23.5 g of boric acid were heated to 150° C. in a round flask with distillation head piece, whereby ethanol distilled off. The mixture was subsequently heated to 175° C. and stirred at this temperature for 4 hours (evolution of carbon dioxide). After completion of the reaction, the mixture was cooled to room temperature, taken up in 500 ml of hexane and washed with 150 ml of 5% (wt./vol.) sodium hydrogen carbonate solution and 100 ml of water. The aqueous phases were back-extracted with 50 ml of hexane. The combined organic phases were dried over sodium sulphate and freed from solvent on a rotary evaporator. Distillation of the resulting crude product in a high vacuum over a Vigreux column gave in the main run 58.6 g (89.6%) of ethyl 4-oxoheptanoate as a colourless liquid; b.p. 50°–56° C./0.2 Torr.

(c) 56.8 g of ethyl 4-oxoheptanoate were dissolved in 150 ml of methanol and treated dropwise within 20 minutes with 18.0 g of hydrazine hydrate, the temperature rising to 38° C. The mixture was boiled at reflux for a further 1.5 hours and then freed from solvent on a rotary evaporator. The residual liquid was taken up in 300 ml of chloroform and washed with 150 ml of water. The aqueous phase was back-extracted three times with 100 ml of chloroform each time. The combined organic phases were dried over sodium sulphate and freed from solvent on a rotary evaporator. The resulting clear oil was taken up in 200 ml of toluene and evaporated up to constant weight on a rotary evaporator. There were thus obtained 48.6 g of 6-propyl-4,5-dihydro-3(2H)-pyridazinone as a slightly coloured oil which presumably still contained water of hydration; b.p. 110°–120° C./0.03 Torr.

(d) 48.6 g of 6-propyl-4,5-dihydro-3(2H)-pyridazinone were dissolved in 90 ml of glacial acetic acid, heated to 70° C. and treated dropwise within 40 minutes with 63.3 g of bromine, the temperature rising to 107° C. and a strong evolution of gas occurring. After completion of the addition of bromine, the mixture was stirred at 80° C. for a further 1 hour, then cooled to room temperature and the glacial acetic acid was removed on a rotary evaporator. The dark oily residue was taken up in 600 ml of water and neutralized firstly with solid sodium hydroxide and then with sodium hydrogen carbonate. An almost black oil separated at the bottom of the vessel. The supernatant turbid solution was separated, stirred with active carbon for 15 minutes at 40° C., suction filtered and rinsed with 100 ml of warm water. The clear filtrate was cooled to room temperature and extracted once with 500 ml of chloroform and twice with 250 ml of chloroform each time. The combined organic phases were dried over sodium sulphate and freed from solvent on a rotary evaporator. The brown coloured crystals obtained were evaporated to dryness three times with 300 ml of toluene each time and then recrystallized from 140 ml of tert.butyl methyl ether at −20° C. 28.0 g of almost white crystals were thus obtained. By concentration of the mother liquor and recrystallization from 36 ml of tert.butyl methyl ether at −20° C. there were obtained a further 8.2 g of light beige crystals. Yield: 36.2 g (78.9%) of 6-propyl-3(2H)-pyridazinone of melting point 51°–60° C.

(e) 11.75 g of 6-propyl-3(2H)-pyridazinone were dissolved in 70 ml of absolute toluene while warming in a sulphonation flask under nitrogen, heated to 80° C. and treated dropwise while stirring well within 30 minutes with a solution of 24.4 g of phosphorus oxybromide in 24.4 g of absolute toluene. The mixture was subsequently stirred under reflux for a further 3 hours. After completion of the reaction, the mixture was poured into 200 ml of water and neutralized with solid sodium hydrogen carbonate. The phases were separated and the aqueous phase was back-extracted twice with 100 ml of tert.butyl methyl ether each time. The combined organic phases were washed with 100 ml of water and dried over sodium sulphate. After evaporation of the solvent, the dark brown crystalline residue (14.1 g) was sublimed at 40°–60° C. in a high vacuum, there being obtained 8.2 g (48%) of 3-bromo-6-propylpyridazine as white crystals of melting point 35°–36° C.

The following compounds were prepared in an analogous manner:
3-[2-(Trans-4-pentylcyclohexyl)ethynyl]-6-methylpyridazine; m.p. (C-I) 92.5°–93° C.,
diethyl 2-hexanoylsuccinate; b.p. 108°–112° C./0.1 Torr,
ethyl 4-oxononanoate, b.p. 75°–80° C./0.2 Torr,
6-pentyl-4,5-dihydro-3(2H)-pyridazinone; m.p. 34° C.,
6-pentyl-3(2H)-pyridazinone, m.p. 40° C.

EXAMPLE 4

8.0 g of 3-bromo-6-propylpyridazine (prepared according to Example 3) were dissolved in 50 ml of triethylamine in a sulphonation flask under nitrogen. The solution was cooled to 0° C., treated with 562 mg of bis-(triphenylphosphine)-palladium (II) dichloride and 76 mg of copper (I) iodide and then treated dropwise within 20 minutes with 7.5 g of trans-1-ethynyl-4-pentylcyclohexane. The mixture was subsequently stirred at 0° C. for several hours, then at room temperature overnight and finally at 50° C. for a further 3 hours. For the working-up, the dark coloured mixture was diluted with 100 ml of tert.butyl methyl ether and suction filtered through a paper filter (rinsing with tert.butyl methyl ether). The filtrate was concentrated on a rotary evaporator. The dark coloured crystalline residue was taken up in 150 ml of tert.butyl methyl ether and washed successively with 100 ml of 2% (wt./vol.) ammonium chloride solution and with 100 ml of water. Each of the aqueous phases were back-extracted with a small amount of tert.butyl methyl ether. The combined organic phases were dried over sodium sulphate and concentrated on a rotary evaporator. For the purification, the brown coloured crystals obtained were chromatographed on silica gel with hexane/ethyl acetate (vol. 2:1), there being obtained a fraction of the desired product 3-[2-(trans-4-pentylcyclohexyl)ethynyl]-6-propylpyridazine (5.2 g) and a mixed fraction consisting of 3-bromo-6-propylpyridazine and product (4.8 g). The pure fraction was recrystallized once from ethanol at −20° C. and once from hexane at −20° C. and finally dried well in a vacuum drying oven at 40° C. There were thus obtained 3.4 g (28.5%) of 3-[2-(trans-4-pentylcyclohexyl)ethynyl]-6-propylpyridazine in the form of white crystals of melting point (C-I) 118.5° C., boiling point 210°-220° C./0.08 Torr.

The trans-1-ethynyl-4-pentylcyclohexane used as the starting material was prepared as follows:

(a) A solution, cooled to −20° C., of 331.6 g of tetrabromomethane in 1 l of dry methylene chloride was treated dropwise under nitrogen gasification within 30 minutes with a solution of 524.6 g of triphenylphosphine in 1 l of methylene chloride. The mixture was subsequently stirred at −5° C. for a further 30 minutes, then treated dropwise at this temperature within 30 minutes with a solution of 91.2 g of trans-4-pentylcyclohexanecarboxaldehyde in 500 ml of methylene chloride and stirred at −5° C. for a further 2 hours. The mixture was poured into 6 l of hexane, the mixture was stirred at −20° C. for 1 hour and then the precipitate was filtered off under suction and washed well with about 1 l of cold (−20° C.) hexane. The filtrate was concentrated to a volume of about 1 l on a rotary evaporator, dilued with 2 l of hexane, again concentrated to a volume of about 1 l and stirred at −20° C. for a further 1 hour. The precipitate was filtered off under suction and rinsed well with about 500 ml of cold (−20° C.) hexane. The filtrate was freed from solvent on a rotary evaporator and the yellow oil obtained was filtered chromatographically on silica gel with about 3 l of hexane. The eluate was evaporated up to constant weight on a rotary evaporator, there being obtained 122.8 g (72.6%) of trans-1-(2,2-dibromovinyl)-4-pentylcyclohexane as a colourless oil; Rf-value (hexane) 0.55.

(b) A solution of 84.5 g of trans-1-(2,2-dibromovinyl)-4-pentylcyclohexane in 800 ml of absolute tetrahydrofuran was cooled to −75° C. under nitrogen gasification and treated dropwise within 30 minutes with 400 ml of an about 1.6M solution of butyl lithium in hexane. The mixture was subsequently stirred at −70° C. for a further 2 hour, then poured into 5.5 l of 2% (wt./vol.) sodium hydrogen carbonate solution and extracted with 1 l of hexane. The aqueous phase was back-extracted with 700 ml of hexane. The combined organic phases were dried over sodium sulphate and freed from solvent on a rotary evaporator. Distillation of the resulting light yellow oil in a high vacuum gave in the main run 40.6 g (91.1%) of trans-1-ethynyl-4-pentylcyclohexane as a colourless liquid which still contained cis-isomer; b.p. 52°-54° C./0.02 Torr. By recrystallization from ethanol at −25° C. and drying up to constant weight at 30° C. in a vacuum drying oven there could be obtained 20.4 g of product free from cis-isomer. From the mother liquor there could be isolated according to the same method a further 6.5 g of product which was almost free from cis-isomer.

EXAMPLE 5

7.8 g of 3-chloro-6-propylpyridazine were dissolved in 30 ml of triethylamine in a sulphonation flask under nitrogen. The solution was cooled to 0° C., treated with 700 mg of bis-(triphenylphosphine)-palladium (II) dichloride and 95 mg of copper (I) iodide and then treated dropwise within 30 minutes with a solution of 8.4 g of trans-1-ethynyl-4-butylcyclohexane in 10 ml of triethylamine. The mixture was subsequently stirred at room temperature for 3 hours and then at 50° C. overnight. For the working-up, the dark coloured mixture was diluted with 150 ml of tert.butyl methyl ether and suction filtered through a paper filter (rinsing with tert.butyl methyl ether). The filtrate was concentrated on a rotary evaporator. The dark coloured crystalline residue was taken up in 150 ml of tert.butyl methyl ether and washed successively with 100 ml of 2% (wt./vol.) ammonium chloride solution and with 100 ml of water. Each of the aqueous phases were back-extracted with a small amount of tert.butyl methyl ether. The combined organic phases were dried over sodium sulphate and concentrated on a rotary evaporator. Distillation of the resulting crude product in a high vacuum gave in the main run (b.p. 190° C./0.05 Torr) 10.2 g of product in the form of yellow crystals. Recrystallization of this product from acetone at −20° C. and working-up of the mother liquor gave a total of 7.6 g of light beige crystals. These were again recrystallized from 22 ml of acetone at −20° C., there being obtained 5.5 g (38.7%) of 3-[2-(trans-4-butylcyclohexyl)ethynyl]-6-propylpyridazine in the form of white crystals of melting point (C-I) 117° C.

The 3-chloro-6-propylpyridazine used as the starting material was prepared as follows:

(a) 46.0 g of phosphorus oxychloride were heated to 60° C. in a sulphonation flask under nitrogen and treated within 1 hour with 27.6 g of 6-propyl-3(2H)-pyridazinone (prepared according to Example 3) in small portions. The mixture was subsequently heated slowly to 100° C. and stirred at this temperature until the reaction was complete according to thin-layer chromatography (about 2 hours). After cooling to room temperature, the dark brown solution was poured into 1 l of water and neutralized with solid sodium hydroxide and sodium hydrogen carbonate. The aqueous phase was subsequently extracted once with 500 ml of tert.butyl methyl ether and then twice with 250 ml of tert.butyl methyl ether each time. The organic phases were washed with 500 ml of water and the aqueous phase was back-extracted twice with 100 ml of tert.butyl methyl ether each time. The combined organic phases were dried over sodium sulphate and freed from solvent on a rotary evaporator. Distillation of the resulting dark brown oil in a high vacuum gave in the main run 22.9 g (73.1%) of 3-chloro-6-propylpyridazine as a colourless liquid; b.p. 72°–74° C./0.4 Torr.

The trans-1-ethynyl-4-butylcyclohexane used as the starting material was prepared as follows:

(b) A solution, cooled to −20° C., of 398 g of tetrabromomethane in 1 l of methylene chloride was treated dropwise under nitrogen gasification within 30 minutes with a solution of 629.6 g of triphenylphosphine in 1 l of methylene chloride. The mixture was subsequently stirred at −10° C. for a further 30 minutes, then treated dropwise within 30 minutes with a solution of 101 g of trans-4-butylcyclohexanecarboxaldehyde in 500 ml of methylene chloride and stirred at −5° C. for a further 2 hours. The mixture was poured into 4 l of hexane, the resulting mixture was stirred at −20° C. for 1 hour and then the precipitate was filtered off under suction and rinsed well with 1 l of cold (−20° C.) hexane. The filtrate was concentrated to a volume of about 1 l on a rotary evaporator, diluted with 2 l of hexane, again concentrated to a volume of about 1 l and stirred at −20° C. for a further 30 minutes. The precipitate was filtered off under suction and rinsed well with 700 ml of cold (−20° C.) hexane. The filtrate was freed from solvent on a rotary evaporator and the resulting yellow oil (195 g) was filtered chromatographically on silica gel with about 3 l of hexane. The eluate was evaporated up to constant weight on a rotary evaporator, there being obtained 171.3 g (88.1%) of trans-1-(2,2-dibromovinyl)-4-butylcyclohexane as a colourless liquid; Rf-value (hexane) 0.55.

(c) A solution of 162.1 g of trans-1-(2,2-dibromovinyl)-4-butylcyclohexane in 1.3 l of absolute tetrahydrofuran was cooled to −75° C. under nitrogen gasification and treated dropwise within 1 hour with 690 ml of a 1.6M solution of butyl lithium in hexane. The mixture was subsequently stirred at −70° C. for a further 2 hours, then poured into 1.5 l of water, neutralized with concentrated hydrochloric acid and extracted twice with 1 l of hexane each time. The combined organic phases were washed with 500 ml of water, dried over sodium sulphate and concentrated to dryness on a rotary evaporator. Distillation of the resulting light yellow crude product in a high vacuum gave in the main run 75.9 g (92.4%) of trans-1-ethynyl-4-butylcyclohexane as a colourless liquid; b.p. 41°–43° C./0.4 Torr.

The following compound was prepared in an analogous manner:

3-Chloro-6-pentylpyridazine; b.p. 82° C./0.04 Torr.

EXAMPLE 6

11.1 g of 3-chloro-6-pentylpyridazine were dissolved in 40 ml of triethylamine in a sulphonation flask under nitrogen. The solution was cooled to 0° C., treated with 840 mg of bis-(triphenylphosphine)-palladium (II) dichloride and 114 mg of copper (I) iodide and then treated portionwise within 30 minutes with a solution of 9.1 g of trans-1-ethynyl-4-pentylcyclohexane in 15 ml of triethylamine. The mixture was subsequently stirred at room temperature overnight, 2.35 g of trans-1-ethynyl-4-pentylpyridazine were then added and the resulting mixture was stirred at 50° C. overnight. For the working-up, the mixture was taken up in 180 ml of tert.butyl methyl ether and suction filtered through a paper filter (rinsing with tert.butyl methyl ether). The filtrate was concentrated on a rotary evaporator. The dark coloured oily residue was taken up in 200 ml of tert.butyl methyl ether and washed twice with 100 ml of water each time. The aqueous phases were back-extracted with 50 ml of tert.butyl methyl ether. The combined organic phases were dried over sodium sulphate and evaporated to dryness on a rotary evaporator. Recrystallization of the resulting crude product from 70 ml of hexane at −20° C. and working-up of the mother liquor gave a total of 14.0 g of beige crystals. These were recrystallized from 42 ml of ethanol at −20° C., there being obtained 10.7 g (45.6%) of 3-[2-(trans-4-pentylcyclohexyl)-ethynyl]-6-pentylpyridazine as light beige crystals of melting point (C-I) 108°–109° C.

EXAMPLE 7

3.6 g of 3-[2-(trans-4-pentylcyclohexyl)ethynyl]-6-propylpyridazine were dissolved in 40 ml of methanol in a round flask, treated with 0.2 g of palladium/carbon (5%) and hydrogenated at room temperature while shaking (hydrogen uptake: 660 ml in about 4 hours). After completion of the reaction, the mixture was suction filtered, the filter residue was rinsed well with methanol and the filtrate was freed from solvent on a rotary evaporator. Bulb-tube distillation of the resulting crude product gave, at 175°–180° C./0.05 Torr, 3.4 g of product in the form of yellowish crystals. These were recrystallized from 15 ml of acetone at −20° C., there being obtained 2.5 g of white crystals. From the mother liquor there was obtained, after concentration and recrystallization from 4 ml of acetone, a further 0.4 g of white crystals. Both crystallizates (2.9 g) were recrystallized from 12.5 ml of acetone at −20° C. The white crystals obtained (2.6 g) were finally dissolved in 50 ml of hexane, filtered, the filtrate was concentrated, the residue was recrystallized from 26 ml of hexane at −20° C. and dried at room temperature overnight in a high vacuum in a slight stream of nitrogen. Yield: 2.3 g (63.9%) of 3-[2-(trans-4-pentylcyclohexyl)ethyl]-6-propylpyridazine in the form of white crystals of melting point 64.2° C.

The following compounds were manufactured in an analogous manner:

3-[2-(Trans-4-butylcyclohexyl)ethyl]-6-propylpyridazine; m.p. 67.5° C.,

3-[2-(trans-4-pentylcyclohexyl)ethyl]-6-pentylpyridazine; m.p. 80.9° C.

EXAMPLE 8

(a) 116.1 g of laevulinic acid were dissolved in 400 ml of methanol and treated dropwise within 15 minutes with 51.0 g of hydrazine hydrate. An exothermic reaction took place and the temperature rose to 53° C. For the completion of the reaction, the mixture was stirred at 60° C. for a further 2 hours, then cooled to room temperature and freed from solvent on a rotary evaporator. The oily residue was evaporated to dryness once with 200 ml of toluene and once with 200 ml of isopropanol. After further drying up to constant weight in a vacuum drying oven at 50° C., there were obtained 109.9 g (98%) of 6-methyl-4,5-dihydro-3(2H)-pyridazinone as pale yellow coloured crystals of melting point 102°–103° C.

(b) A solution of 112.1 g of 6-methyl-4,5-dihydro-3(2H)-pyridazinone in 300 ml of glacial acetic acid was warmed to 40° C. and then treated dropwise without additional warming within 1.5 hours with 199.8 g of bromine. An exothermic reaction took place and the temperature rose to 80° C. After the addition of somewhat more than half of the bromine, a white precipitate began to crystallize out. The mixture was stirred at 80° C. for a further 3 hours, then cooled to room temperature, diluted with 300 ml of ethyl acetate and suction filtered (rinsing with 250 ml of ethyl acetate). The yellow coloured crystals were suspended in 250 ml of water and the suspension was neutralized with 100 ml of 28% (wt./vol.) sodium hydroxide solution and solid sodium hydrogen carbonate, diluted with 50 ml of water and heated on a steam-bath until the crystals had dissolved completely. The product crystallized out again by slowly cooling to 0° C. The product was filtered off under suction, rinsed well with 200 ml of cold water and dissolved while heating in 300 ml of methanol. The solution was filtered and the filtrate was cooled slowly to −20° C. The product which crystallized out was filtered off under suction and washed with cold methanol. Concentration of the mother liquor and recrystallization of the residue from 100 ml of methanol at −20° C. gave further product. Both crystallizates were dried up to constant weight at 60° C. in a vacuum drying oven, there being obtained 87.7 g (79.6%) of 6-methyl-3(2H)-pyridazinone as white crystals of melting point 141°–142° C.

(c) 34.5 g of phosphorus oxychloride were heated to 70° C. under nitrogen and treated within 1 hour with 16.5 g of 6-methyl-3(2H)-pyridazinone in small portions. After completion of of the addition, the temperature was increased to 90° C. and the mixture was stirred for about a further 2 hours. For the working-up, the dark brown solution was poured into 300 ml of water, stirred well and neutralized with solid sodium hydroxide and sodium hydrogen carbonate. The aqueous phase was subsequently extracted continuously overnight with 500 ml of hexane. The organic phase was separated and freed from solvent. The brown coloured crystals obtained were sublimed from a bath heated at 50°–60° C. There were thus obtained 12.8 g (66.4%) of 3-chloro-6-methylpyridazine as white crystals of melting point 59°–60° C.

EXAMPLE 9

A solution of 18.6 g of phosphorus oxybromide in 18.6 g of absolute toluene was diluted with 100 ml of absolute toluene in a sulphonation flask under nitrogen, heated to 65° C. and treated dropwise within 1.5 hours with a solution of 21.6 g of 6-pentyl-3(2H)-pyridazinone (prepared according to Example 3) in 100 ml of absolute toluene. A grey coloured difficultly stirrable suspension formed occasionally. For the completion of the reaction, the mixture was stirred at 65° C. overnight (18 hours), then cooled to room temperature, poured into 250 ml of water and stirred well. The aqueous phase was neutralized with 28% (wt./vol.) sodium hydroxide solution and with sodium hydrogen carbonate. The organic phase was separated and the aqueous phase was back-extracted with 100 ml of tert.butyl methyl ether. The combined organic phases were washed with 100 ml of water, dried over sodium sulphate and evaporated on a rotary evaporator. The brown coloured crude product was subsequently distilled in a high vacuum, there being obtained 21.4 g (72%) of 3-bromo-6-pentylpyridazine in the form of a brown oil (b.p. 99°–108° C./0.04–0.06 Torr) which crystallized upon cooling.

Recrystallization of a sample from methyl formate at −20° C. gave white crystals of melting point 31°–32° C.

We claim:

1. A compound of the formula

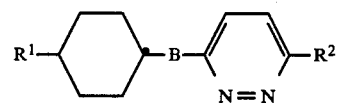

I wherein B is —C≡C— or —CH$_2$CH$_2$—, R$^1$ is straight-chain C$_1$–C$_{12}$-alkyl and R$^2$ is straight-chain C$_1$–C$_{12}$-alkyl or straight-chain C$_1$–C$_{12}$-alkoxy.

2. The compound of claim 1, wherein B is —CH$_2$CH$_2$—.

3. The compound of claim 1 wherein B is —C≡C—.

4. The compound of claim 1, wherein R$^2$ is straight-chain C$_1$–C$_{12}$-alkyl.

5. The compound of claim 4, wherein R$^2$ is straight-chain C$_1$–C$_7$-alkyl.

6. The compound of claim 1, wherein R$^2$ is straight-chain C$_1$–C$_6$-alkoxy.

7. The compound of claim 1 wherein R$^1$ is straight-chain C$_3$–C$_7$-alkyl.

8. The compound of claim 1, wherein the compound has the formula:

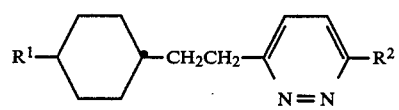

Ia wherein R$^1$ is straight-chain C$_3$–C$_7$-alkyl and R$^2$ is straight-chain C$_1$–C$_7$-alkyl or straight-chain C$_1$–C$_6$-alkoxy.

9. The compound of claim 1, wherein the compound has the formula

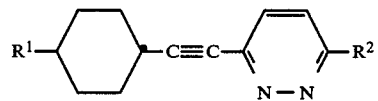

Ib wherein R$^1$ is straight-chain C$_3$–C$_7$-alkyl and R$^2$ is straight-chain C$_1$–C$_7$-alkyl or straight-chain C$_1$–C$_6$-alkoxy.

10. A liquid crystalline mixture comprising
(a) a compound of the formula

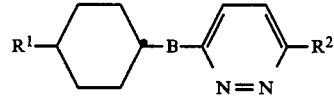

I wherein B is —C≡C— or —CH$_2$CH$_2$—, R$^1$ is straight-chain C$_1$–C$_{12}$-alkyl and R$^2$ is straight-chain C$_1$–C$_{12}$-alkyl or straight-chain C$_1$–C$_{12}$-alkoxy; and
(b) a liquid crystalline carrier material.

11. The liquid crystalline mixture of claim 10, wherein the liquid crystalline carrier material has a dielectric anisotropy of at most +1.

12. The liquid crystalline mixture of claim 10, comprising three components A, B and C, each of which contains at last one compound, wherein component A has a viscosity of at most 40 cp, a clearing point of at least 40° C. and a dielectric anisotropy between −2 and +1;
component B has a dielectric anisotropy below −2 and contains at least one compound of formula I; and
component C has a dielectric anisotropy above +10, a clearing point of at least 100° C. and cross-over frequency in the total mixture of at most 15 kHz at 20° C.

13. An electro-optical cell comprising:
(a) two plate means;
(b) liquid crystal means disposed between the two plate means and including a compound of the formula

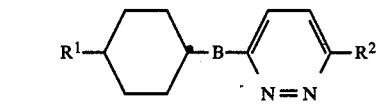

wherein B is —C≡C— or —CH$_2$CH$_2$—, R$^1$ is straight-chain C$_1$–C$_{12}$-alkyl and R$^2$ is straight-chain C$_1$–C$_{12}$-alkyl or straight-chain C$_1$–C$_{12}$-alkoxy; and
(c) means for applying an electrical potential to said plate means.

14. The compound of claim 1, 3-[2-(trans-4-pentylcyclohexyl)-ethyl]-6-propylpyridazine.

15. The compound of claim 1, 3-[2-(trans-4-butylcyclohexyl)-ethyl]-6-propylpyridazine.

16. The compound of claim 1, 3-[2-(trans-4-pentylcyclohexyl)-ethyl]-6-pentylpyridazine.

* * * * *